US011771778B2

(12) United States Patent
Assaf et al.

(10) Patent No.: US 11,771,778 B2
(45) Date of Patent: Oct. 3, 2023

(54) USING DREADD FOR NEURONAL MODULATION IN TREATING NEURONAL DISEASES

(71) Applicants: Fadi Assaf, Miilya Village (IL); Yitzhak Schiller, Haifa (IL)

(72) Inventors: Fadi Assaf, Miilya Village (IL); Yitzhak Schiller, Haifa (IL)

( * ) Notice: Subject to any disclaimer, the term of this patent is extended or adjusted under 35 U.S.C. 154(b) by 384 days.

(21) Appl. No.: 16/078,491

(22) PCT Filed: Mar. 8, 2017

(86) PCT No.: PCT/IL2017/050294
§ 371 (c)(1),
(2) Date: Aug. 21, 2018

(87) PCT Pub. No.: WO2017/153995
PCT Pub. Date: Sep. 14, 2017

(65) Prior Publication Data
US 2019/0083652 A1 Mar. 21, 2019

Related U.S. Application Data

(60) Provisional application No. 62/305,601, filed on Mar. 9, 2016.

(51) Int. Cl.
*A61K 48/00* (2006.01)
*C07K 14/705* (2006.01)
*A61P 25/14* (2006.01)
*A61K 31/5513* (2006.01)
*A61P 25/16* (2006.01)
*C12N 15/113* (2010.01)
*C12N 15/62* (2006.01)
*C12N 15/85* (2006.01)
*A61K 38/00* (2006.01)

(52) U.S. Cl.
CPC ...... *A61K 48/0016* (2013.01); *A61K 31/5513* (2013.01); *A61K 48/005* (2013.01); *A61K 48/0058* (2013.01); *A61K 48/0075* (2013.01); *A61P 25/14* (2018.01); *A61P 25/16* (2018.01); *C07K 14/705* (2013.01); *C12N 15/113* (2013.01); *C12N 15/62* (2013.01); *C12N 15/8509* (2013.01); *A61K 38/00* (2013.01); *C12N 2750/14143* (2013.01)

(58) Field of Classification Search
CPC ............ A61K 48/0016; A61K 31/5513; A61K 48/005; A61K 48/0058; A61K 48/0075; A61K 38/00; A61P 25/14; A61P 25/16; C07K 14/705; C12N 15/113; C12N 15/62; C12N 15/8509; C12N 2750/14143
USPC ...................................................... 424/93.2
See application file for complete search history.

(56) References Cited

U.S. PATENT DOCUMENTS 6,780,409 B2  8/2004 During et al.
2018/0193414 A1* 7/2018 Greenberg ........... C12N 15/861

FOREIGN PATENT DOCUMENTS

EP        3349760 A1    7/2018

OTHER PUBLICATIONS

Vazey et al. "New tricks for old dogmas: optogenetic and designer receptor insights for Parkinson's disease." Brain research 1511 (2013): 153-163 (Year: 2013).*
Jenner. "Wearing off, dyskinesia, and the use of continuous drug delivery in Parkinson's disease." Neurologic clinics 31.3 (2013): S17-S35 (Year: 2013).*
Benabid et al. "Deep brain stimulation of the subthalamic nucleus for the treatment of Parkinson's disease." The Lancet Neurology 8.1 (2009): 67-81 (Year: 2009).*
Elena M. Vazey et al: "Designer receptors: therapeutic adjuncts to cell replacement therapy in Parkinson's disease". The Journal of Clinical Investigation; Jul. 2014; vol. 124; No. 7; pp. 2858-2860.
Fadi Assaf et al: "A chemogenetic approach for treating experimental Parkinson's disease". Movement Disorders; Apr. 2019; vol. 34; No. 4; pp. 469-479.
Cendra Agulhon et al: "Modulation of the autonomic nervous system and behaviour by acute glial cell Gq protein-coupled receptor activation in vivo", The Journal of Physiology, Neuroscience, vol. 591, No. 22, Nov. 15, 2013, pp. 5599-5609.
Xinwei Li et al: "Acetic Acid Activates the AMP-Activated Protein Kinase Signaling Pathway to Regulate Lipid Metabolism in Bovine Hepatocytes", PLoS One, vol. 8, No. 7, Jul. 4, 2013, pp. 1-10.
Hiroshi Yagi et al: "A Synthetic Biology Approach Reveals a CXCR4-G13-Rho Signaling Axis Driving Transendothelial Migration of Metastatic Breast Cancer Cells", Science Signaling, vol. 4, No. 191, Sep. 20, 2011, pp. 1-24.
Alcacer, C. et al: "Role of striatal projection neurons in the generation of L-DOPA-induced dyskinesia", Parkinsonism & Related Disorders, vol. 22, e90, Jan. 1, 2016.
Filion, M. et al: "Effects of dopamine agonists on the spontaneous activity of globus pallidus neurons in monkeys with MPTP-induced parkinsonism", Brain research, vol. 547, No. 1, pp. 152-161, Dec. 31, 1991.
Vazey, E. M. et al: "New tricks for old dogmas: optogenetic and designer receptor insights for Parkinson's disease", Brain research, vol. 1511, pp. 153-163, May 20, 2013.

(Continued)

*Primary Examiner* — Janet L Epps-Smith
*Assistant Examiner* — Alexander W Nicol
(74) *Attorney, Agent, or Firm* — The Roy Gross Law Firm, LLC; Roy Gross

(57) ABSTRACT

A method for treating a patient suffering from a neuronal hypo-kinetic disease or a neuronal hyper-kinetic disease by modulating neuronal activity in the: internal globus pallidus (GPi), in the anterior motor thalamus and/or in the external globus pallidum (GPe) and/or in the subthalamic nucleus (STN) by utilizing suppressor and/or enhancer DREADDs is provided.

8 Claims, 20 Drawing Sheets

(56) References Cited

OTHER PUBLICATIONS

Aston-Jones, G. et al: "Recent advances in optogenetics and pharmacogenetics", Brain research, vol. 1511, pp. 1-5, May 20, 2013.
Indirect pathway of movement, URL: https://en.wikipedia.org/wiki/Indirect_pathway_of_movement; Jan. 25, 2016.
International Search Report PCT/IL2017/050294 Completed May 10, 2017; dated Jun. 1, 2017 3 pages.
Written Opinion of the International Searching Authority PCT/IL2017/050294 dated Jun. 1, 2017 7 pages.

* cited by examiner

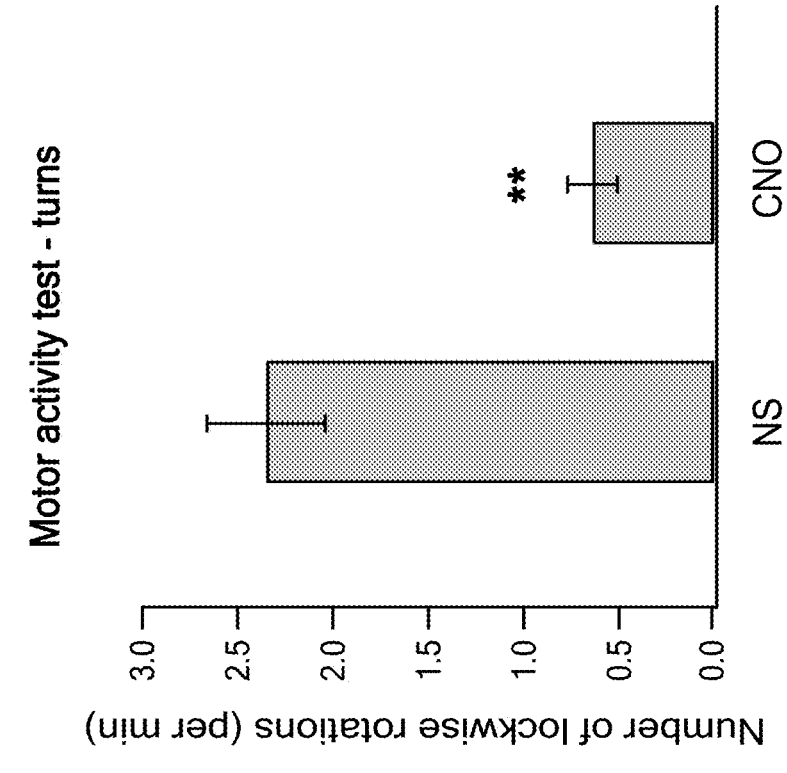
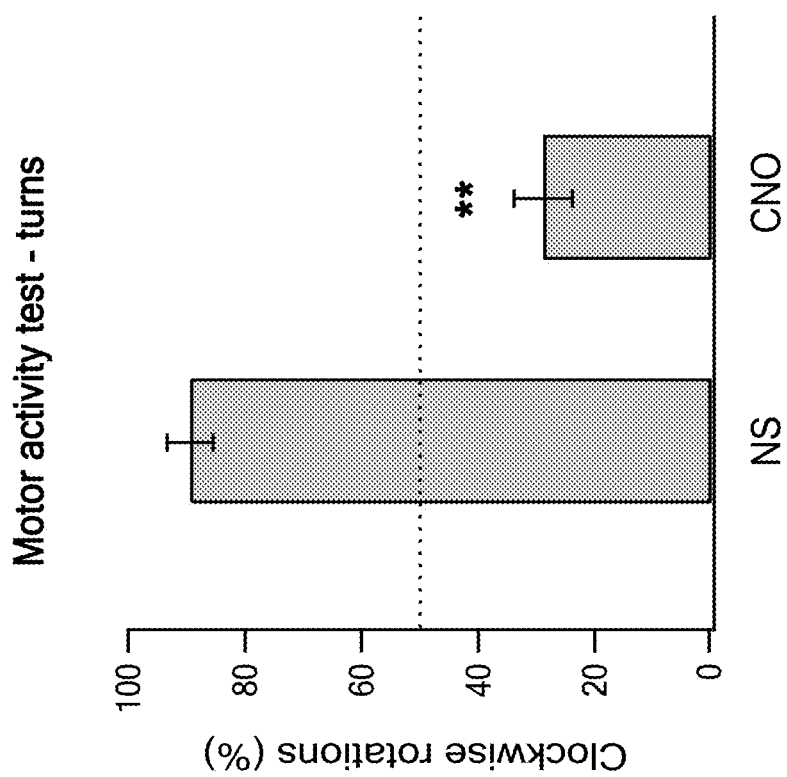
FIG. 2A
FIG. 2B

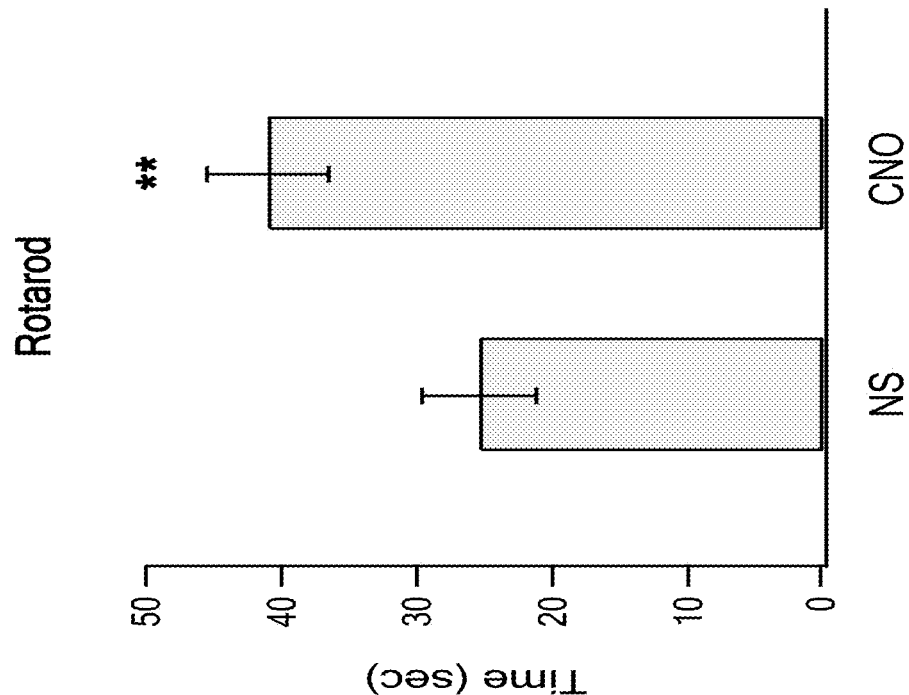
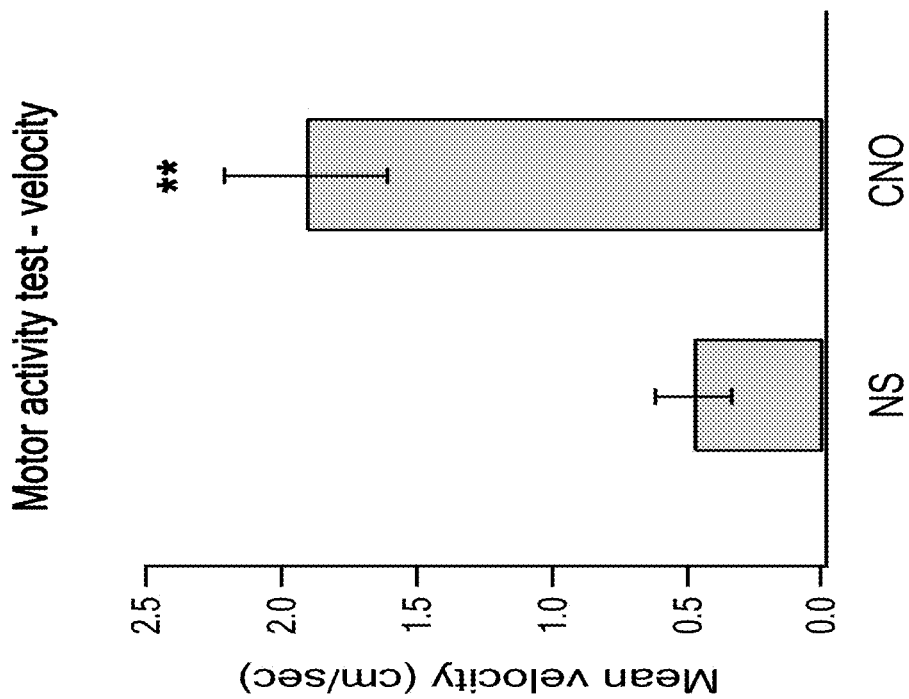
FIG. 3A
FIG. 3B

USING DREADD FOR NEURONAL MODULATION IN TREATING NEURONAL DISEASES

RELATED APPLICATIONS

This application is a National Phase of PCT Patent Application No. PCT/IL2017/050294 having International filing date of Mar. 8, 2017, which claims the benefit of priority of U.S. Patent Application No. 62/305,601 filed on Mar. 9, 2016. The contents of the above applications are all incorporated by reference as if fully set forth herein in their entirety.

FIELD OF THE INVENTION

A method for treating a neuronal hypo-kinetic disease or a neuronal hyper-kinetic disease by utilizing suppressor and/or enhancer DREADDs is provided.

BACKGROUND OF THE INVENTION

Several novel strategies using engineered receptors activated by synthetic ligands or by light have ushered in a new era of brain research that allows for precise experimental manipulation of neuronal activity. These techniques are now being used to probe the involvement of discrete brain circuits in complex behaviors (Ferguson and Neumaier, 2012).

One such approach uses designer receptors exclusively activated by designer drugs (DREADDs) to modulate cellular functions (Rogan and Roth, 2011). This family of evolved muscarinic receptors has been shown to increase (Gs-DREADD; Gq-DREADD) or decrease (Gi/o-DREADD) cellular activity following administration of an otherwise inert synthetic ligand, clozapine-n-oxide (Armbruster et al, 2007). When packaged into viral vectors or expressed in transgenic mouse models, these tools allow cellular activity to be controlled in a defined spatial and temporal manner. For example, activation of hippocampal neurons by Gq-DREADD receptors amplifies γ-rhythms and increases locomotor activity and stereotypy in mice (Alexander et al, 2009). Activity of non-neuronal cells can also be controlled by DREADD receptors, as expression and activation of either Gs-DREADD or Gq-DREADD receptors in pancreatic β-cells increases insulin release, and repeated activation of these receptors leads to β-cell hypertrophy (Guettier et al, 2009).

DREADDs are mutant muscarinic receptors. A: DREADDs are formed by point mutations in the third and fifth transmembrane regions of muscarinic receptors (Y149C and A239G in hM3). In addition, the Gs-coupled DREADD contains the second and third intracellular loops of the β1-AR in place of those of the M3 muscarinic receptor. B: in human pulmonary artery smooth muscle cells, the hM3Dq receptor (hM3D) is selectively activated by CNO but not by ACh, resulting in PIP2 hydrolysis. Conversely, the wild-type M3 muscarinic receptor (hM3) is potently activated by ACh but not by CNO (Armbruster et al., 2007).

DREADD receptor technology was used in a cell-specific manner to unravel the role of striatal circuits in neuropsychiatric disorders, such as drug addiction and obsessive-compulsive disorder. Viral vectors that use neuropeptide promoters (dynorphin or enkephalin) were used to target DREADD receptor expression to specific cell populations in the striatum (striatonigral versus striatopallidal neurons, respectively). Some results indicated that transiently decreasing activity of striatopallidal neurons in rats during repeated amphetamine exposure facilitated the development of behavioral sensitization, whereas disrupting activity of striatonigral neurons impaired the persistence of this phenomenon (Ferguson et al, 2011). Thus, these findings clearly demonstrate that striatonigral and striatopallidal neurons have critical, yet opposing, roles in the regulation of drug experience-dependent behavioral plasticity.

DREADDs have also been used to control glial cell activity to modulate the autonomic nervous system (Agulhon et al., 2013). In periphery, DREADDs have been used to control GPCR signaling in pancreatic beta-cells (Guettier et al., 2009), hepatocytes (Li et al., 2013), and breast cancer cells (Yagi et al., 2011).

A hypo-kinetic disorder or hypokinesia refers to decreased bodily movement. Hypokinesia is characterized by a partial or complete loss of muscle movement due to a disruption in the basal ganglia. Patients with hypokinetic disorders like Parkinson's disease (PD) experience muscle rigidity and an inability to produce movement. It is also associated with mental health disorders and prolonged inactivity due to illness, amongst other diseases.

A hyper-kinetic disorder or hyperkinesias (or hyperkinesis), refers to an increase in muscular activity that can result in excessive abnormal movements, excessive normal movements, or a combination of both. Hyperkinesia is a state of excessive restlessness which is featured in a large variety of disorders that affect the ability to control motor movement, such as Huntington's disease. Many hyperkinetic movements are the result of improper regulation of the basal ganglia-thalamocortical circuitry. In many instances hyperkinesia is paired with hypotonia, a decrease in muscle tone. Many hyperkinetic disorders are psychological in nature and are typically prominent in childhood.

SUMMARY OF THE INVENTION

In one embodiment, this invention provides a method for treating a subject afflicted with a neuronal hypo-kinetic disease or disorder, comprising: suppressing neuronal activity in the internal globus pallidus (GPi); and enhancing neuronal activity in the anterior motor thalamus, the subthalamic nucleus (STN) or the external globus pallidus (GPe), wherein suppressing neuronal activity comprises transfecting GPi neurons with an inhibitory DREADD and activating the inhibitory DREADD, wherein enhancing neuronal activity comprises transfecting neurons in the anterior motor thalamus, in the subthalamic nucleus (STN) or the external globus pallidus (GPe), with and excitatory DREADD and activating the excitatory DREADD, thereby treating a subject afflicted with a neuronal hypo-kinetic disease or disorder.

In another embodiment, transfecting GPi neurons with an inhibitory DREADD is injecting AAV viral vector comprising the Gi DREAD gene.

In another embodiment, transfecting neurons in the anterior motor thalamus, in the subthalamic nucleus (STN) or the external globus pallidus (GPe), with an excitatory DREADD is injecting AAV viral vector comprising the: Gq DREAD gene, Gs DREAD gene, or both.

In another embodiment, suppressing neuronal activity in the internal globus pallidus (GPi) and enhancing neuronal activity in the anterior motor thalamus, in the subthalamic nucleus (STN) or the external globus pallidus (GPe) are preformed concomitantly.

In another embodiment, this invention further provides that activating inhibitory DREADD, activating excitatory DREADD, or both is contacting GPi neurons, anterior motor thalamus neurons, STN neuron, the external globus pallidus (GPe) or any combination thereof with CNO. In another embodiment, a hypo-kinetic disease or disorder is Parkinson's disease (PD).

In another embodiment, this invention further provides a method for treating a subject afflicted with a neuronal hyper-kinetic disease or disorder, comprising: enhancing neuronal activity in the internal globus pallidus (GPi); and suppressing neuronal activity in the anterior motor thalamus, in the subthalamic nucleus (STN) or the external globus pallidus (GPe), wherein enhancing neuronal activity comprises transfecting GPi neurons with an excitatory DREADD and activating excitatory DREADD, wherein suppressing neuronal activity comprises transfecting neurons in the anterior motor thalamus in the subthalamic nucleus (STN) or the external globus pallidus (GPe), with an inhibitory DREADD and activating inhibitory DREADD, thereby treating a subject afflicted with a neuronal hyper-kinetic disease or disorder.

In another embodiment, transfecting GPi neurons with an excitatory DREADD is injecting AAV viral vector comprising the: Gq DREAD gene, Gs DREAD gene, or both. In another embodiment, transfecting neurons in the anterior motor thalamus, in the subthalamic nucleus (STN) or the external globus pallidus (GPe) with an inhibitory DREADD is injecting AAV viral vector comprising the Gi DREAD gene or transfecting neurons in the GPi with an excitatory DREADD (Gq) is injecting AAV viral vector.

In another embodiment, a neuronal hyper-kinetic disease or disorder is chorea, dystonia, tick-disorder, Tourette syndrome, obsessive compulsive disorder, or any combination thereof.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 2A-2D. Are bar graphs showing the effect of Unilateral Gi DREADDs in the GPi (EP) and SNr—effect of CNO on mice with 6OHDA induced hemi PD and expressing the Gi DREADD in the EP and SNr nuclei. The effect of blinded CNO administration was compared to NS on three behavioral parameters: the number and percent of clockwise rotations in a 5-minute motor activity test (FIG. 2A and FIG. 2B); the mean velocity in a motor activity test (FIG. 2C); and the average time mice remained on the rotating rod in the rotarod test (FIG. 2D). The beneficial effect of CNO on all behavioral parameters examined. ** $p<0.01$.

FIGS. 3A-3B. Are bar graphs showing the effect of bilateral Gi DREADDs in the GPi (EP) and SNr—the effect of CNO on 6OHDA induced bilateral PD expressing the Gi DREADD in both EP and SNr nuclei. The effect of blinded CNO administration was compared to NS on two behavioral parameters: The mean velocity in a motor activity test (FIG. 3A); and the average time mice remained on the rotating rod in the rotarod test (FIG. 3B). The beneficial effect of CNO on both the mean velocity and rotarod test. ** $p<0.01$.

Figure 9B:
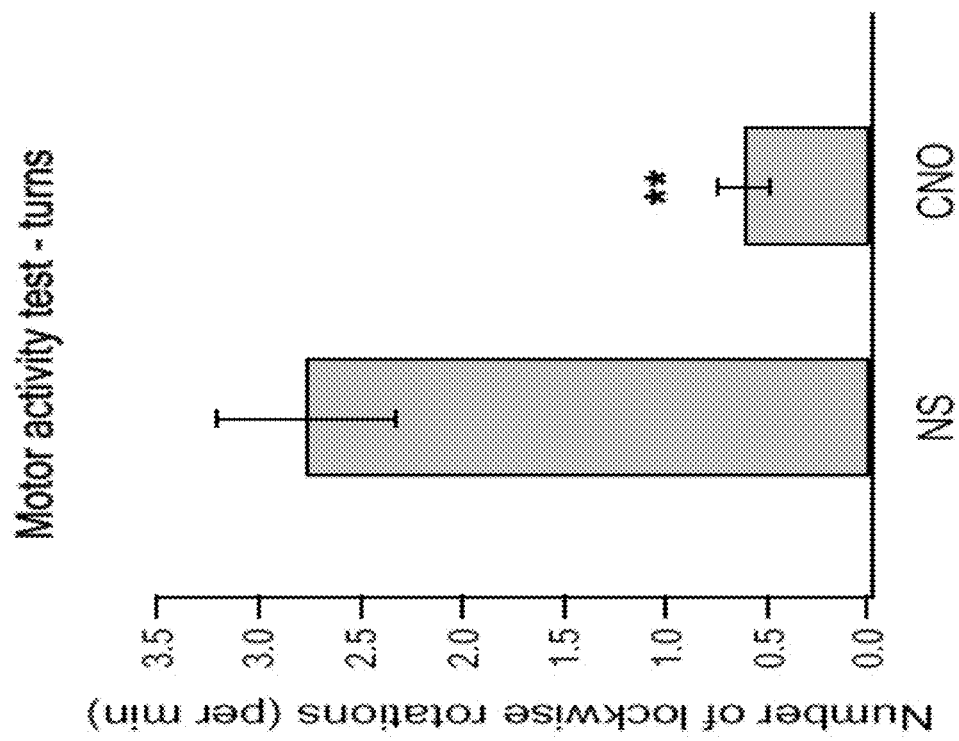
FIGS. 9A-9D. Are bar graphs showing unilateral Gi DREADDs in the GPi (EP) and SNr: Continues 5 day activation—the suppression of the indirect pathway by a 5-day activation of Gq DREADDs in the GPe of 6OHDA induced PD mice. Open field and Rota-Rod tests were performed during 5-day application of normal saline (NS)
Figure 9A:
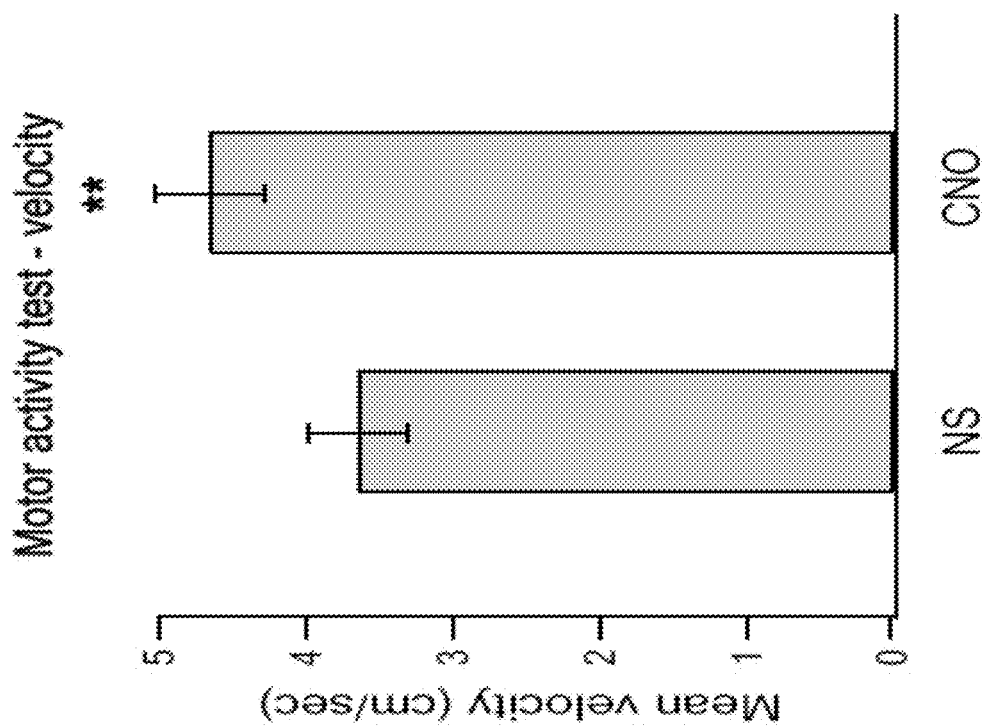
Figure 9C:
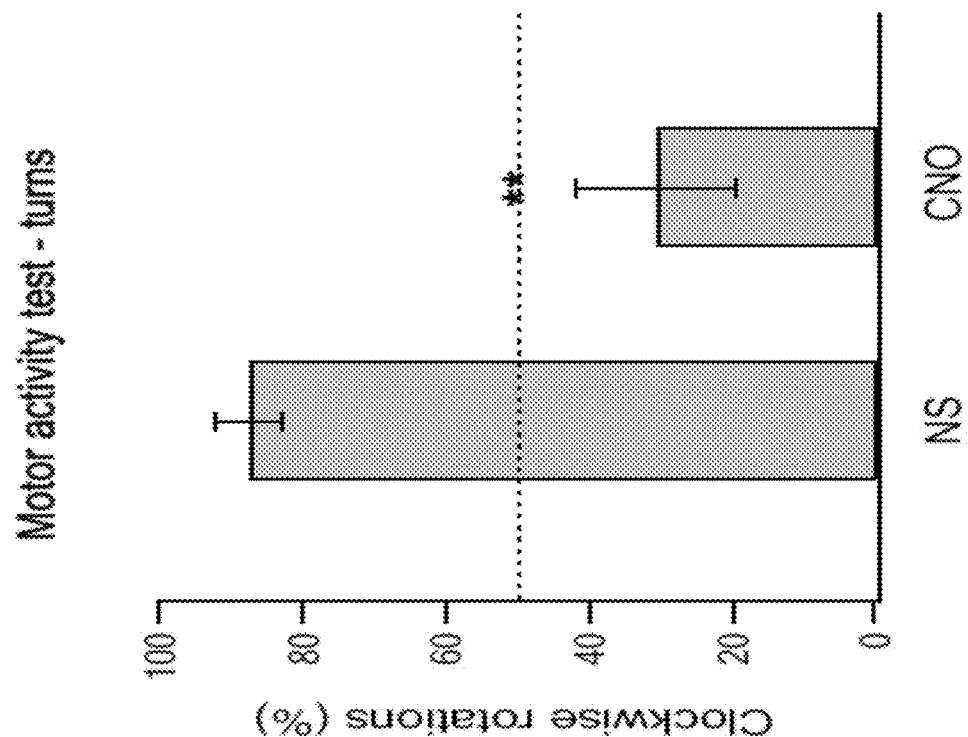
Figure 9D:
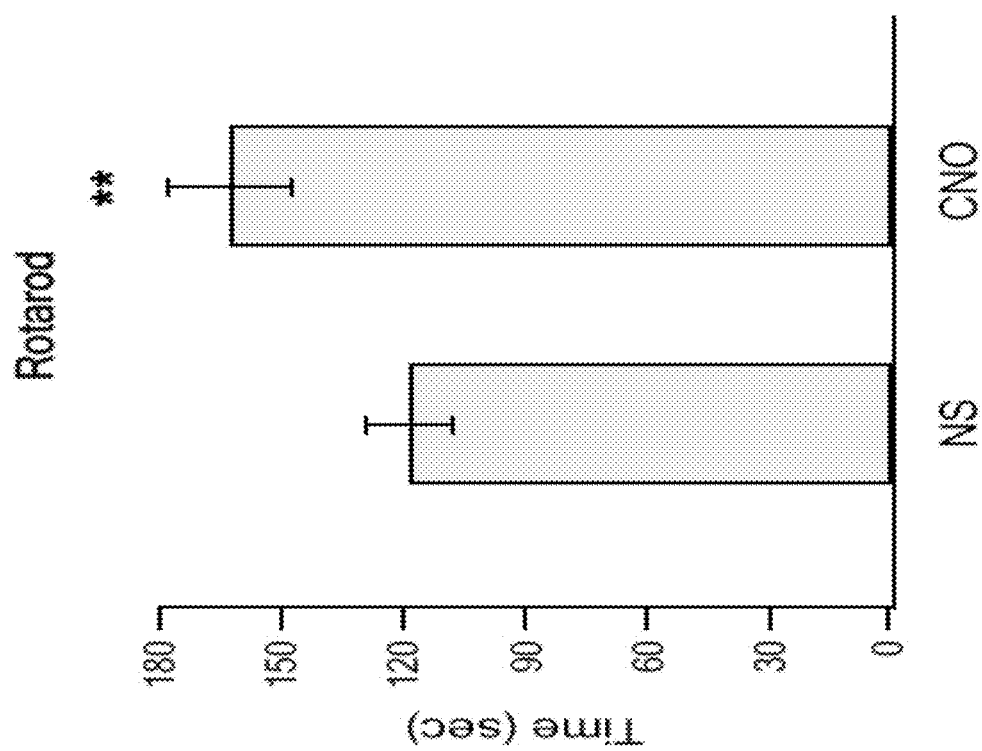
Figure 10A:
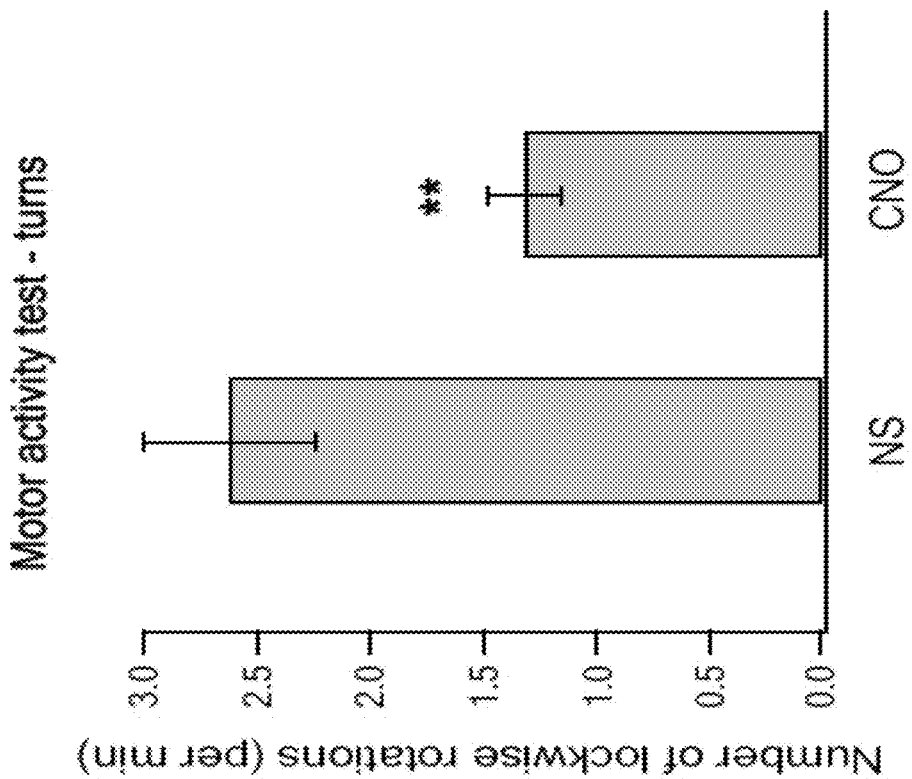
Figure 10B:
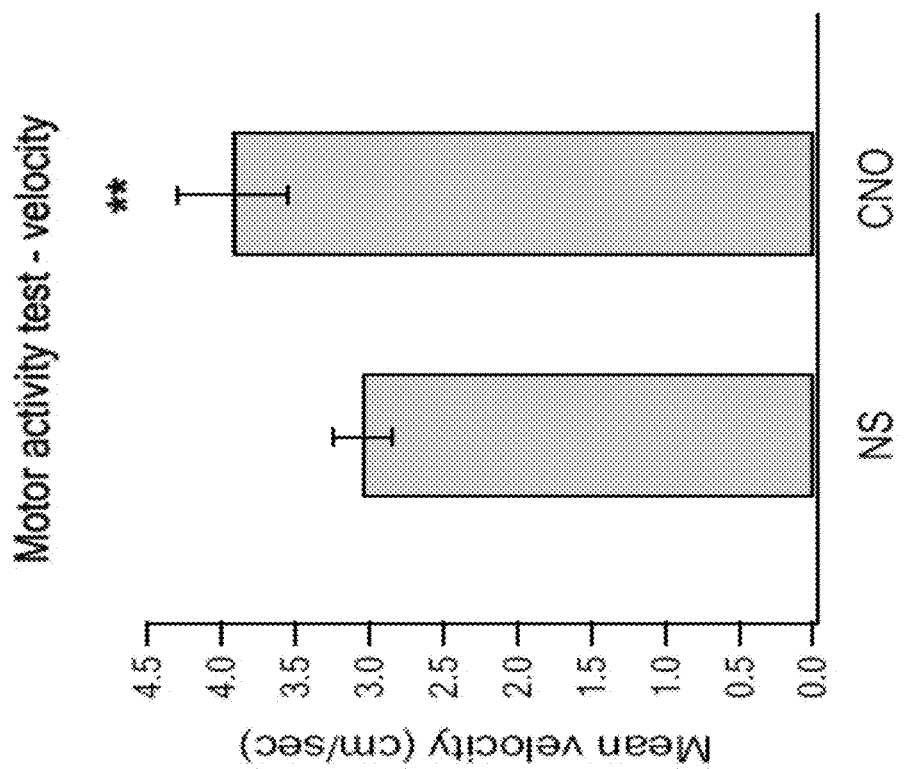
Figure 10D:
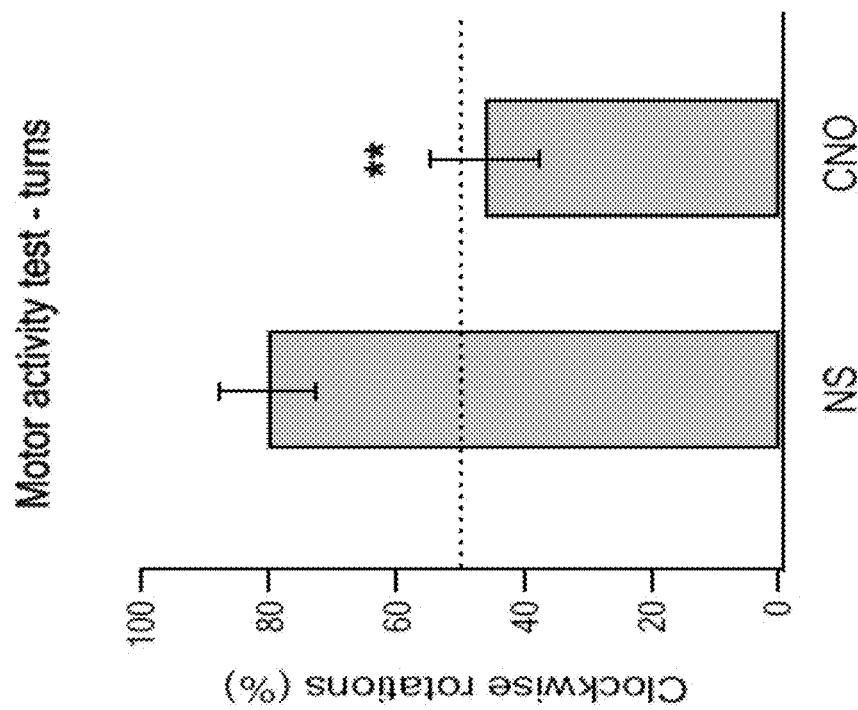
Figure 10C:
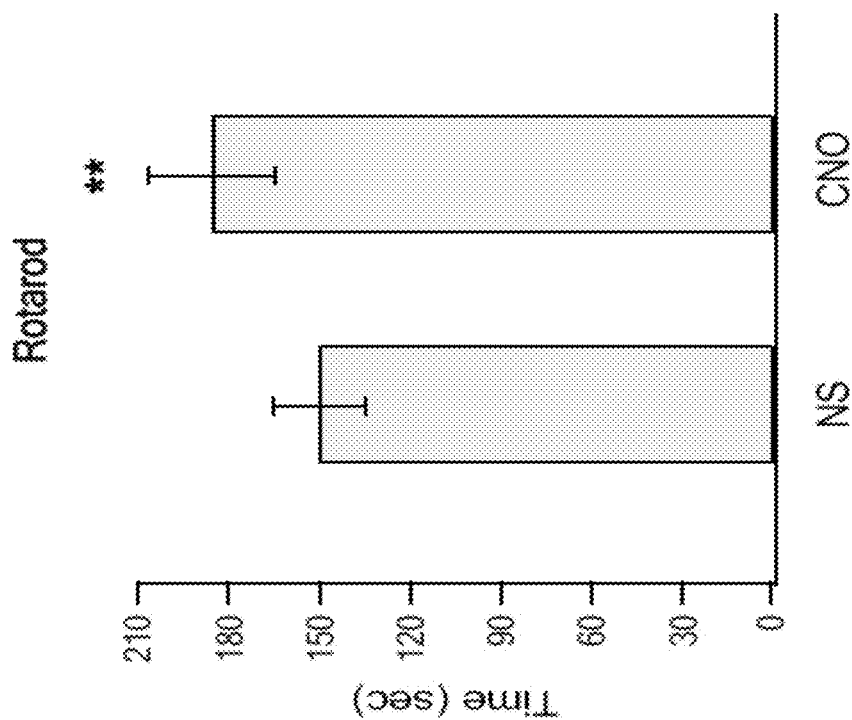
Figure 11A:
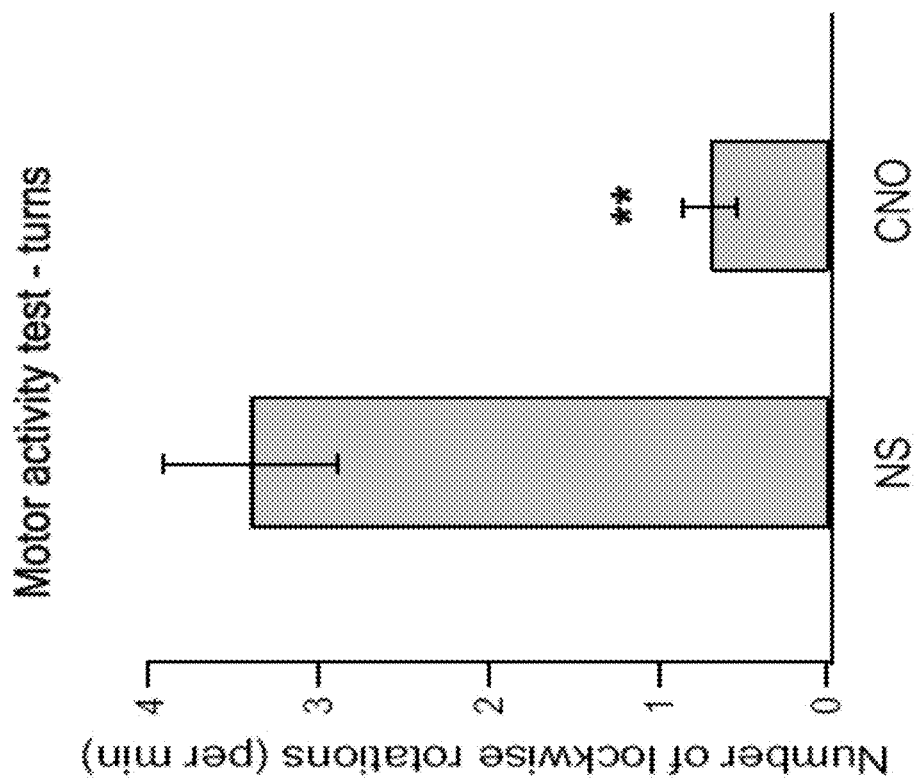
Figure 11B:
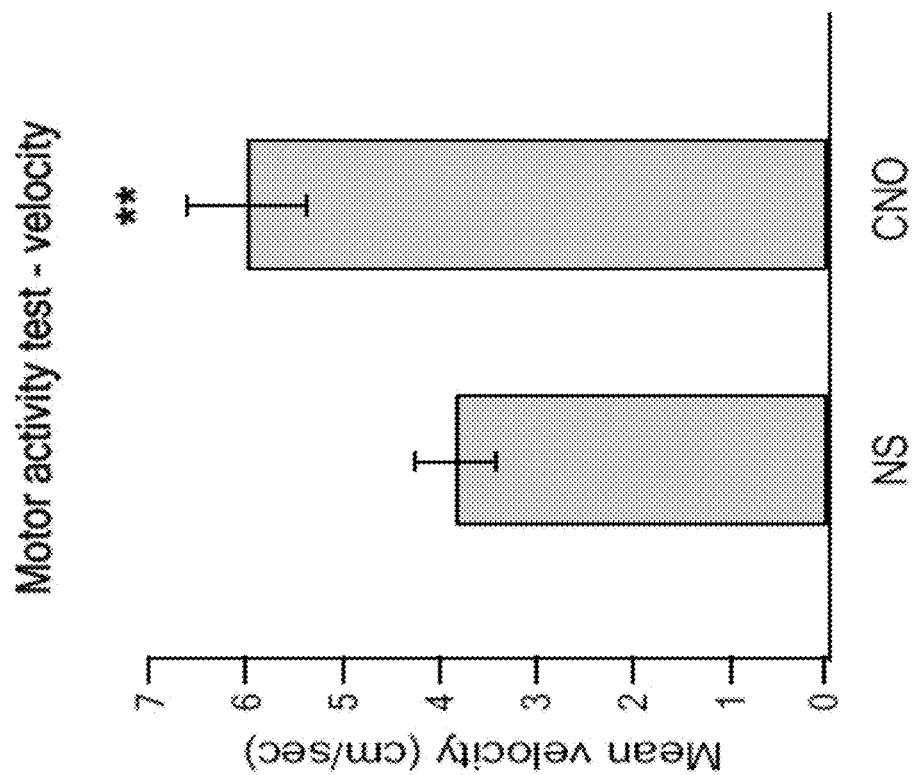
Figure 11D:
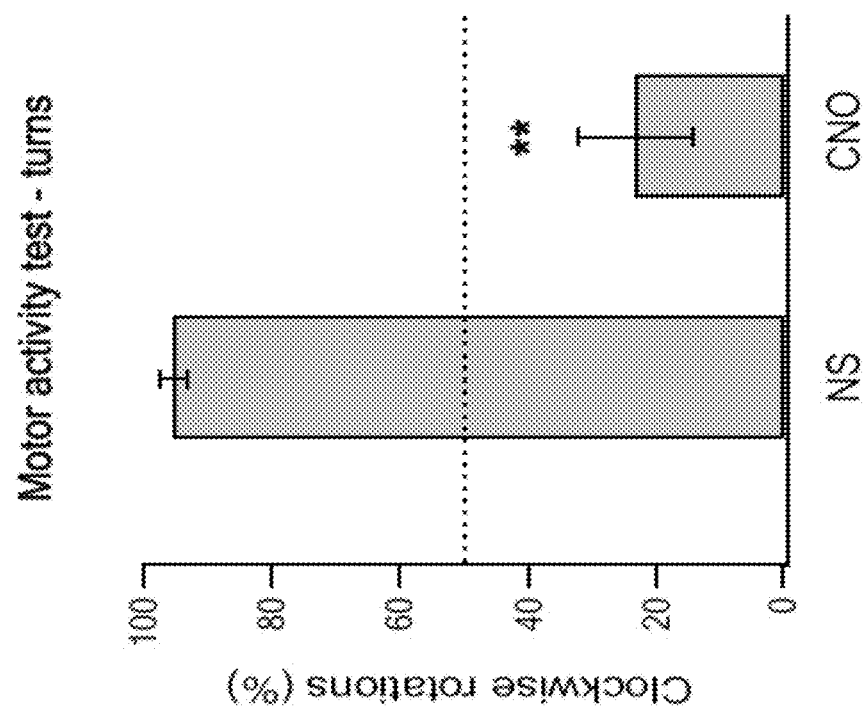
Figure 11C:
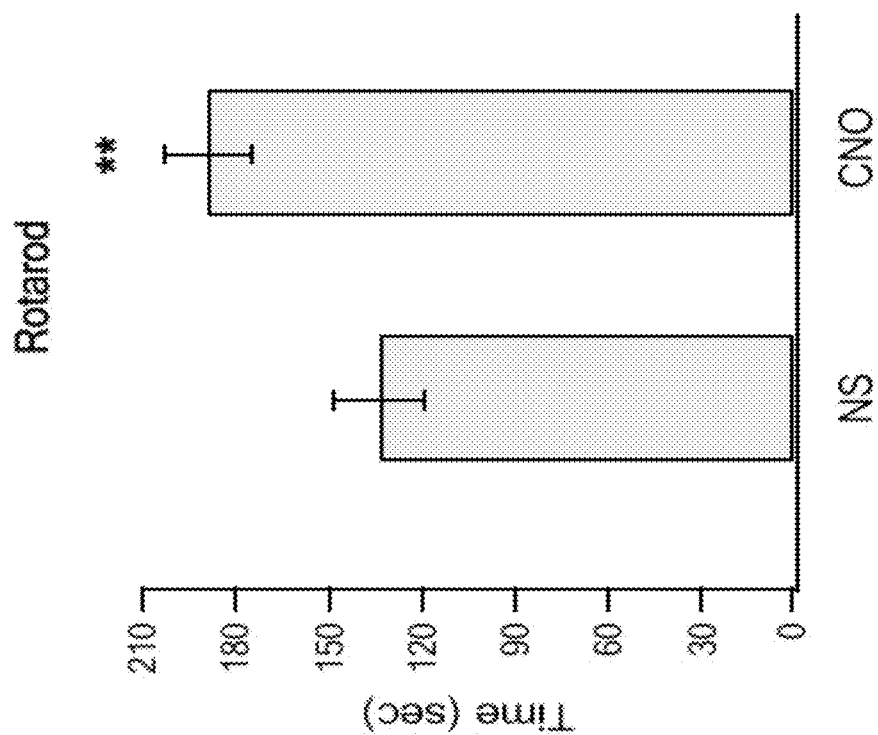

and CNO in 6-OHDA treated PD mice expressing the Gq DREADDs in the GPe nucleus unilaterally. Average (mean±SEM) of the movement velocity (FIG. 9A), Rota-Rod score (FIG. 9B), number (FIG. 9C) and percent (FIG. 9D) of clockwise rotations in NS and CNO treated unilateral PD mice (n=6). ** p<0.01.

FIGS. 10A-10D. Are bar graphs showing unilateral Gq DREADDs in the GPe: Continues 5-day activation—a 5-day suppression of the activity of the output basal ganglia nuclei in 6OHDA induced PD mice. Open field and Rota-Rod tests were performed during 5-day application of normal saline (NS) and CNO in 6-OHDA treated PD mice expressing the Gi DREADDs in the GPi and SNR nuclei unilaterally. Average (mean±SEM) of the movement velocity (FIG. 10A), Rota-Rod score (FIG. 10B), number (FIG. 10C) and percent (FIG. 10D) of clockwise rotations in NS and CNO treated unilateral PD mice (n=6). ** p<0.01.

FIGS. 11A-11D. Are bar graphs showing a combined unilateral Gi DREADDs in the EP (GPi) and SNr and Gq DREADDs in the GPe and SNr: continuous—a 5-day combined manipulation 3 targets within the basal ganglia nuclei in 6OHDA induced PD mice. Open field and Rota-Rod tests were performed during Gi DREADDs in the GPi and SNR nuclei, Gq DREADDs in the GPe nucleus and a 5-day application of normal saline (NS) and CNO in 6-OHDA treated PD mice expressing the Gq DREADDs in the STN nucleus unilaterally. Average (mean±SEM) of the movement velocity (FIG. 11A), Rota-Rod score (FIG. 11B), number (FIG. 11C) and percent (FIG. 11D) of clockwise rotations in NS and CNO treated unilateral PD mice (n=6). ** p<0.01.

DETAILED DESCRIPTION OF THE INVENTION

The present invention provides, in one embodiment, a method for modulating bodily movement in a subject in need thereof by affecting neuronal activity in the internal globus pallidus (GPi), the external globus pallidus (GPe), the anterior motor thalamus, the subthalamic nucleus (STN), or any combination thereof. In one embodiment, provided a method for improving the motor performance and/or function in a subject afflicted with a neurological or a CNS disease which limits a motor function. In one embodiment, provided a method for improving the motor performance and/or function in a subject afflicted with a neurological or a CNS disease which limits a motor function by targeting and modulating the indirect pathway anatomically (GPe nucleus).

In one embodiment, enhancing STN activity by Gq DREADDs results in restoring and/or significantly improving motor performance of motor activities in a subject afflicted with a neuronal hypo-kinetic disease as demonstrated in both Hemi- and bilateral experimental PD. In one embodiment, it was unexpectedly found that activation of both GPe and STN yielded the same behavioral outcome, as the GPe inhibits the STN. In one embodiment, it was unexpectedly found that activation of both GPe and STN yielded significant improvement of motor performance in a subject afflicted with a neuronal hypo-kinetic disease such as but not limited to PD. In one embodiment, it was unexpectedly found that DREADDs modulation of three targets within the basal ganglia complex, the indirect pathway nucleus GPe, the output nuclei GPi and SNr and the STN resulted in significant improvement of motor performance in a subject afflicted with a neuronal hypo-kinetic disease such as but not limited to PD.

In one embodiment, provided herein a method for significantly improving motor performance in a subject afflicted with a neuronal hypo-kinetic disease (such as PD) via DREADDs modulation of three targets within the basal ganglia complex, the indirect pathway nucleus GPe, the output nuclei GPi and SNr and the STN.

In another embodiment, the term "modulating" is altering. In another embodiment, the term "modulating" is activating, enhancing, restoring, ameliorating or any combination thereof. In another embodiment, the term "modulating" is inhibiting. In another embodiment, the term "modulating" is increasing. In another embodiment, the term "modulating" is inducing. In another embodiment, the term "modulating" is elevating. In another embodiment, the term "modulating" is reducing. In another embodiment, the term "modulating" is differentially activating. In another embodiment, the term "modulating" is decreasing. In another embodiment, the term "modulating" is differentially inhibiting.

In another embodiment, "modulating bodily movement" is modulating the frequency of at least one movement. In another embodiment, "modulating bodily movement" is modulating the amplitude of at least one movement.

In one embodiment, the present invention provides a method for treating a subject afflicted with a neuronal hypo-kinetic disease or disorder, comprising: a. suppressing neuronal activity in the internal globus pallidus (GPi); and b. enhancing neuronal activity in the anterior motor thalamus, the external globus pallidus (GPe) the subthalamic nucleus (STN), wherein suppressing neuronal activity comprises transfecting GPi neurons with an inhibitory DREADD and activating inhibitory DREADD, wherein enhancing neuronal activity comprises transfecting neurons in the anterior motor thalamus, the external globus pallidus (GPe) or in the subthalamic nucleus (STN) with and excitatory DREADD and activating excitatory DREADD, thereby treating a subject afflicted with a neuronal hypo-kinetic disease or disorder.

In another embodiment, DREADD, inhibitory DREADD, excitatory DREADD or any combination thereof is: hM3Dq coupled to Gaq (Gq) signaling and induces firing of neurons; hM4Di coupled to Gai signaling and mediates neuronal and synaptic silencing; and rM3Ds coupled to Gas signaling and which modulates neuronal activity. In another embodiment, inhibitory DREADD is hM4Di, which coupled to Gai (Gi) signaling and mediates neuronal and synaptic silencing. In another embodiment, excitatory DREADD is hM3Dq, coupled to Gaq (Gs) signaling. In another embodiment, excitatory DREADD is rM3Ds, which is coupled to Gas signaling.

In another embodiment, DREADD as described herein is carried by a vector for express in a neuronal target tissue or cells. In another embodiment, DREADD as described herein is carried by a viral vector for express in a neuronal target tissue or cells. In another embodiment, DREADD carried by a viral vector is sufficiently expressed in a neuronal target tissue or cells within 4 to 31 days. In another embodiment, DREADD carried by a viral vector is sufficiently expressed in a neuronal target tissue or cells within 7 to 25 days. In another embodiment, DREADD carried by a viral vector is sufficiently expressed in a neuronal target tissue or cells within 10 to 25 days. In another embodiment, DREADD carried by a viral vector is sufficiently expressed in a neuronal target tissue or cells within 7 to 21 days.

In another embodiment, any DREADD as described herein is activated by CNO. In another embodiment, any DREADD as described herein is activated by CNO administered via parenteral administration. In another embodiment, any DREADD as described herein is activated by CNO administered via oral administration.

In another embodiment, DREADDs are activated by clozapine-N-oxide (CNO). In another embodiment, are activated by clozapine-N-oxide (CNO) at a dosage of between 0.1 to 20 mg/kg. In another embodiment, DREADDs are activated by clozapine-N-oxide (CNO) at a dosage of between 1 to 5 mg/kg.

In another embodiment, the present invention provides that transfecting a GPi neuron with an inhibitory DREADD is contacting a Gi DREAD gene with a GPi neuron. In another embodiment, the present invention provides that transfecting GPi neurons with an inhibitory DREADD is injecting AAV viral vector comprising the Gi DREAD gene. In another embodiment, the present invention provides that transfecting neurons in the anterior motor thalamus and/or in the subthalamic nucleus (STN) and/or the external globus pallidus (GPe) with an excitatory DREADD include injecting AAV viral vector comprising the: Gq DREAD gene, Gs DREAD gene, or both.

In another embodiment, the present invention provides that transfecting neurons in the anterior motor thalamus with an excitatory DREADD include contacting AAV viral vector comprising the: Gq DREAD gene, Gs DREAD gene, or both with neurons in the anterior motor thalamus. In another embodiment, the present invention provides that transfecting neurons in the subthalamic nucleus with an excitatory DREADD include contacting AAV viral vector comprising the: Gq DREAD gene, Gs DREAD gene, or both with neurons in the subthalamic nucleus. In another embodiment, the present invention provides that transfecting neurons in the GPe with an excitatory DREADD include contacting AAV viral vector comprising the: Gq DREAD gene, Gs DREAD gene, or both with neurons in the Gpe. In another embodiment, contacting AAV viral vector comprises injecting AAV viral vector to the neuronal site as described herein. In another embodiment, contacting AAV viral vector comprises injecting AAV viral vector into neurons as described herein.

In another embodiment, the present invention provides that suppressing neuronal activity in the internal globus pallidus (GPi) and enhancing neuronal activity in the anterior motor thalamus, and/or in the external globus pallidum (GPe), and/or in the subthalamic nucleus (STN) are preformed concomitantly. In another embodiment, the present invention provides that CNO administration suppresses neuronal activity in the internal globus pallidus (GPi) and enhances neuronal activity in the anterior motor thalamus and/or in the subthalamic nucleus (STN), and/or in the external globus pallidum (GPe) at once and/or concomitantly. In another embodiment, the present invention provides that activating an inhibitory DREADD and activating an excitatory DREADD is achieved by a single ligand such as but not limited to CNO. In another embodiment, the present invention provides that activating an inhibitory DREADD is achieved by a first ligand and activating an excitatory DREADD is achieved by a second ligand. In another embodiment, the first ligand and the second ligand do not cross react.

In another embodiment, activating the inhibitory DREADD, activating the excitatory DREADD, or both is contacting GPi neurons expressing DREADD, anterior motor thalamus neurons expressing DREADD, STN neuron expressing DREADD, GPe neurons expressing DREADDs or any combination thereof with CNO.

In one embodiment, enhancing STN activity by Gq DREADDs results in restoring and/or significantly improving motor performance of both Hemi- and bilateral experimental PD. In one embodiment, it was unexpectedly found that activation of both GPe and STN yielded the same behavioral outcome, as the GPe inhibits the STN. In one embodiment, it was unexpectedly found that activation of both GPe and STN yielded significant improvement of motor performance in PD. In one embodiment, it was unexpectedly found that DREADDs modulation of three targets within the basal ganglia complex, the indirect pathway nucleus GPe, the output nuclei GPi and SNr and the STN resulted in significant improvement of motor performance PD mice.

In one embodiment, DREADDs modulation of: the indirect pathway nucleus GPe, the output nuclei GPi and SNr and the STN improves and/or restores motor function in a subject afflicted with a disease such as described In another embodiment, treating a subject afflicted with hypo-kinetic disease or disorder is improving motor activities in the subject. In another embodiment, a hypo-kinetic disease is a cardiovascular disease. In another embodiment, a hypo-kinetic disease is a form of cancer. In another embodiment, a hypo-kinetic disease is associated with back pain. In another embodiment, a hypo-kinetic disease is associated with disability arising from the back. In another embodiment, a hypo-kinetic disease is obesity. In another embodiment, a hypo-kinetic disease is type 2 diabetes. In another embodiment, a hypo-kinetic disease is osteoporosis. In another embodiment, a hypo-kinetic disease is osteoarthritis. In another embodiment, a hypo-kinetic disease is associated with a mental disease. In another embodiment, a hypo-kinetic disease is high Blood pressure.

In another embodiment, a subject afflicted with hypo-kinetic disease is afflicted with hypokinesia or decreased bodily movement. In another embodiment, a subject afflicted with hypo-kinetic disease is suffering from damage to the basal ganglia.

In another embodiment, a subject afflicted with hypo-kinetic disease is suffering from a partial loss of muscle movement due to a disruption in the basal ganglia. In another embodiment, a subject afflicted with hypo-kinetic disease is suffering from a complete loss of muscle movement due to a disruption in the basal ganglia. In another embodiment, a subject afflicted with hypo-kinetic disease is afflicted with Parkinson's disease (PD). In another embodiment, a subject afflicted with hypo-kinetic disease experiences muscle rigidity and an inability to produce movement.

In another embodiment, a subject afflicted with hypo-kinetic disease is suffering from akinesia or a severe case of Parkinson's disease. In another embodiment, a subject afflicted with hypo-kinetic disease is suffering from bradykinesia or "stone face" (expressionless face). In another embodiment, a subject afflicted with hypo-kinetic disease is suffering from dysarthria. In another embodiment, a subject afflicted with hypo-kinetic disease is suffering from dyskinesia. In another embodiment, a subject afflicted with hypo-kinetic disease is suffering from dystonia. In another embodiment, a subject afflicted with hypo-kinetic disease is suffering from freezing characterized by an inability to move muscles in any desired direction. In another embodiment, a subject afflicted with hypo-kinetic disease is suffering from neuroleptic malignant syndrome. In another embodiment, a subject afflicted with hypo-kinetic disease is suffering from supranuclear palsy. In another embodiment, a subject afflicted with hypo-kinetic disease is suffering from an increase in muscle tone. In another embodiment, a subject afflicted with hypo-kinetic disease is suffering from 'Cogwheel' rigidity. In another embodiment, a subject afflicted with hypo-kinetic disease is suffering from 'leadpipe' rigidity. In another embodiment, a subject afflicted with hypo-kinetic disease is suffering from postural instability.

In another embodiment, "treating" is reducing muscle rigidity. In another embodiment, "treating" is reducing muscle rigidity. In another embodiment, "treating" is increasing the range of motion of at least one limb. In another embodiment, "treating" is increasing the range of motion of at least one organ. In another embodiment, "treating" is alleviating symptoms associated with a hypo-kinetic disease or disorder.

In one embodiment, DREADD is used to modulate the activity of a nucleus within the cortico-basal ganglia loop. In one embodiment, DREADD is used to counterbalance network abnormalities caused by a disease as described herein (such as but not limited to PD). In one embodiment, DREADD is used for increasing motor activity is subjects afflicted with a disease as described herein. In one embodiment, DREADD is used for reducing basal ganglia output activity.

In one embodiment, DREADD is a Gq DREADD. In one embodiment, DREADD is a Gi DREADD. In one embodiment, a nucleus is the external globus pallidum (GPe) nucleus. In one embodiment, a nucleus is the subthalamic nucleus (STN). In one embodiment, a nucleus is internal globus pallidum (GPi).

In another embodiment, "treating" is reducing alterations of cerebral circulation. In another embodiment, "treating" is reducing blood flow in the supramarginal gyms and angular gyms of the parietal lobe. In another embodiment, "treating" is reducing cardiac activity and changes in the tonus of the heart vessels. In another embodiment, "treating" is alleviating non-motor symptoms associated with Parkinson's disease.

In another embodiment, "treating" is alleviating neuropsychiatric disturbances. In another embodiment, "treating" is alleviating cognitive disturbances. In another embodiment, "treating" is improving visuospatial difficulties. In another embodiment, "treating" is reducing the risk of dementia. In another embodiment, "treating" is reducing the frequency and/or severity of behavior and mood alterations. In another embodiment, "treating" is alleviating depression. In another embodiment, "treating" is alleviating apathy. In another embodiment, "treating" is alleviating anxiety. In another embodiment, "treating" is reducing the risk of psychotic symptoms. In another embodiment, "treating" is reducing the risk of hallucinations or delusions. In another embodiment, "treating" is alleviating the sleep impairment. In another embodiment, "treating" is reducing the risk of orthostatic hypotension. In another embodiment, "treating" is reducing the risk of oily skin. In another embodiment, "treating" is reducing the risk of excessive sweating. In another embodiment, "treating" is reducing the risk of urinary incontinence. In another embodiment, "treating" is reducing the risk of sexual dysfunction. In another embodiment, "treating" is reducing the risk of gastric dysmotility. In another embodiment, "treating" is reducing the risk of eye and vision abnormalities such as decreased blink rate, dry eyes, deficient ocular pursuit (eye tracking) and saccadic movements (fast automatic movements of both eyes in the same direction). In another embodiment, "treating" is reducing difficulties in directing gaze upward. In another embodiment, "treating" is reducing the risk of blurred or double vision. [In another embodiment, "treating" is reducing the risk of impaired sense of smell. In another embodiment, "treating" is reducing the risk of sensation of pain. In another embodiment, "treating" is reducing the risk of paresthesia (skin tingling and numbness). In another embodiment, "treating" is reducing side effects associated with permanent damage to the brain. In another embodiment, "treating" is free of causing permanent damage to the brain by the treatment of the invention.

In another embodiment, enhancing neuronal activity is increasing neuronal frequency. In another embodiment, enhancing neuronal activity is increasing neuronal input, output or both. In another embodiment, enhancing neuronal activity is increasing an action potential. In another embodiment, enhancing neuronal activity is enhancing the rate at which neurons fire. In another embodiment, enhancing neuronal activity is increasing the activity of a neuron. In another embodiment, enhancing neuronal activity is inducing the activity of a neuron. In another embodiment, enhancing neuronal activity is generating oscillatory activity. In another embodiment, neuronal activity is measured by any method or means known to one of skill in the art.

In another embodiment, suppressing neuronal activity is decreasing neuronal frequency. In another embodiment, suppressing neuronal activity is decreasing neuronal input, output or both. In another embodiment, suppressing neuronal activity is decreasing an action potential. In another embodiment, suppressing neuronal activity is decreasing the rate at which neurons fire. In another embodiment, suppressing neuronal activity is decreasing the activity of a neuron. In another embodiment, suppressing neuronal activity is inhibiting oscillatory activity.

In another embodiment, the present invention provides a method for treating a subject afflicted with a neuronal hyper-kinetic disease or disorder, comprising: a. enhancing neuronal activity in the internal globus pallidus (GPi); and b. suppressing neuronal activity in the anterior motor thalamus or the external globus pallidus (GPe) or in the subthalamic nucleus (STN), wherein enhancing neuronal activity comprises transfecting GPi neurons with an excitatory DREADD and activating the excitatory DREADD, wherein suppressing neuronal activity comprises transfecting neurons in the anterior motor thalamus or in the subthalamic nucleus (STN), or in the external globus pallidum (GPe) with an inhibitory DREADD and activating the inhibitory DREADD, thereby treating a subject afflicted with a neuronal hyper-kinetic disease or disorder.

In another embodiment, transfecting GPi neurons with an excitatory DREADD is injecting AAV viral vector comprising the: Gq DREAD gene, Gs DREAD gene, or both. In another embodiment, transfecting neurons in the anterior motor thalamus or the external globus pallidum (GPe) or in the subthalamic nucleus (STN) with an inhibitory DREADD is injecting AAV viral vector comprising the Gi DREAD gene. In another embodiment, enhancing neuronal activity in the internal globus pallidus (GPi) and suppressing neuronal activity in the anterior motor thalamus or the external globus pallidum (GPe) or in the subthalamic nucleus (STN) are performed at once and/or concomitantly. In another embodiment, activating inhibitory DREADD and activating excitatory DREADD is achieved by a single ligand such as but not limited to CNO.

In another embodiment, treating a subject afflicted with a neuronal hyper-kinetic disease or disorder or a neuronal hypo-kinetic disease or disorder is improving motor activities in the subject. In another embodiment, treating a subject afflicted with a neuronal hyper-kinetic disease or disorder is without inducing permanent damage to the brain.

In another embodiment, a hyper-kinetic disease or disorder is hyperkinesias or hyperkinesis. In another embodiment, a hyper-kinetic disease is Huntington's disease. In another embodiment, a hyper-kinetic disease further comprises hypotonia. In another embodiment, a hyper-kinetic disease or disorder is chorea, dystonia, tick-disorder, Tourette syndrome, hemi balism, or any combination thereof. In another embodiment, a hyper-kinetic disease or disorder is athetosis. In another embodiment, a hyper-kinetic disease or disorder is an ataxia. In another embodiment, a hyper-kinetic disease or disorder is Hemiballismus.

In another embodiment, a hyper-kinetic disease or disorder is Tardive dyskinesia. In another embodiment, a hyper-kinetic disease or disorder includes stereotypies. In another embodiment, a hyper-kinetic disease or disorder includes myoclonus. In another embodiment, a hyper-kinetic disease or disorder includes hemifacial spasm. In another embodiment, a hyper-kinetic disease or disorder includes tardive dystonia. In another embodiment, a hyper-kinetic disease or disorder is Wilson's disease. In another embodiment, a hyper-kinetic disease or disorder includes volitional hyperkinesias. In another embodiment, a hyper-kinetic disease or disorder includes tremor. In another embodiment, a hyper-kinetic disease or disorder includes restless leg syndrome.

In another embodiment, a hyper-kinetic disease or disorder includes post-stroke repercussions.

In another embodiment, a hyper-kinetic disease or disorder includes dentatorubral-pallidoluysian Atrophy.

In one embodiment, a subject afflicted with a neuronal hypo-kinetic disease such as PD is treated according to the methods described herein by modifying the activity of different nuclei in the basal ganglia loop. In one embodiment, altering the activity of different nuclei in the basal ganglia loop is achieved by using Designer Receptors Exclusively Activated by Designer Drugs (DREADD) (example 2). In one embodiment, provided herein a method for reducing the output of the inhibitory GPi and SNr nuclei to the ventral thalamus. In one embodiment, provided herein a method for increasing the excitatory drive to the neocortex.

In one embodiment, provided herein a method for improving the motor symptoms of PD by targeting three different nuclei in the basal ganglia loop: the GPi and SNr nuclei, which serve as the output nuclei of the basal ganglia loop; the GPe, which is exclusively involved in the indirect pathway; and the STN, which serves as the main target for deep brain stimulation (DBS) in PD patients. In one embodiment, the invention provides the inhibition of neuronal firing in inhibitory output nuclei (the GPi and SNr nuclei). In one embodiment, the invention provides the inhibition of neuronal firing in inhibitory output nuclei (the GPi and SNr nuclei) via Gi DREADDS. In one embodiment, the invention provides the activation of Gi expressed in the STN. In one embodiment, treating PD or inhibiting a side effect associated with PD comprises the activation of Gq DREADDS expressed in the STN. In one embodiment, treating PD or inhibiting a side effect associated with PD comprises the bilateral Gq activation. In one embodiment, treating is increasing, restoring or enhancing a motor activity.

In one embodiment, a "physiologically acceptable carrier" and/or a "pharmaceutically acceptable carrier" are combined with a DREADD activator such as CNO. In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered modulator. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Oral administration, in one embodiment, comprises a unit dosage form comprising tablets, capsules, lozenges, chewable tablets, suspensions, emulsions and the like. Such unit dosage forms comprise a safe and effective amount of the desired modulator, or modulators. The pharmaceutically-acceptable carriers suitable for the preparation of unit dosage forms for peroral administration are well-known in the art.

In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjutants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets.

In some embodiments, compositions for use in the methods of this invention comprise solutions or emulsions, which in some embodiments are aqueous solutions or emulsions comprising a safe and effective amount of the modulator of the present invention and optionally, other compounds.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In another embodiment, a modulator is delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In one embodiment, compositions of the present invention are presented in a pack or dispenser device, such as an FDA approved kit, which contain one or more unit dosage forms containing the modulator. In one embodiment, the pack, for example, comprise metal or plastic foil, such as a blister pack. In one embodiment, the pack or dispenser device is accompanied by instructions for administration. In one embodiment, the pack or dispenser is accommodated by a U.S. Food and Drug Administration for prescription drugs or of an approved product notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the insert.

In one embodiment, it will be appreciated that the modulator of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

EXAMPLES

Material and Methods
Animals
Adult C57 black mice are used the current experiments.
Vector
DREADDs are provided within viral particles. Viral particles injected in-situ.
Two viral vectors are used AAV-hSyn-hM3D(Gq)-mCherry and the AAV-hSyn-hM4D(Gi)-mCherry. The viruses are injected with a stereotactic apparatus to the targeted brain region (either GPi, thalamus, GPe or subthalamic nucleus).
Parkinson Model
The 6OHDA model was used.
Behavioral Test
To monitor the motor impairment and the ability of the DREADD therapy to reverse these impairments the following behavioral tests are conducted. Open field test: to measure motor activity dysfunction. In this test the spontaneous movement of mice in a square arena are recorded and quantified. Rotarod test: Mice were placed on a rotating rod with rotation speed gradually increasing from 4 to 40 RPM using a preset acceleration program. The time mice fell from the rotating rod was measured, with 300 seconds being the maximal time measured on the rod.

Example 1: DREADDs Impact in Hyperkinesia and Hypokinesia

C57 black mice are injected with the viral vector (either AAV-hSyn-hM3D(Gq)-mCherry which contains the gene for the excitatory DREADD Gq or AAV-hSyn-hM4D(Gi)-mCherry which contains the gene for the inhibitory DREADD (Gi) is injected into the targeted brain regions (either GPi, GPe, STN or anterior thalamus alone or in combination). Injections are performed using a micro-injector mounted on a stereotactic apparatus. After viral intraperitoneal injections 6OHDA is administered (streotactic injections) to generate the experimental Parkinsonian mice.

Approximately 3 weeks after induction of experimental Parkinson's disease by 6OHDA, behavioral experiments are performed. The DREADD molecule (either Gq, Gi or both) is activated by IP injection of CNO. In these experiments, the behaviors of Parkinsonian mice under control conditions (no injections), injection of CNO and sham injection of saline are compared.

The motor performance of mice is monitored in the open field test, the Rotarod test.

The following DREADD containing viral vector injections are performed:
1) The Gi DREADD is injected into the GPi bilaterally. 2) The Gq DREADD are injected into the thalamus bilaterally. 3) Either the Gi or the Gq DREADD are injected into the STN bilaterally. 4). The Gq DREADD is injected into the GPe bilaterally.

Moreover, viral vectors containing DREADDs are simultaneously injected into two separate brain regions to obtain synergistic effects: 1) The Gi DREADD is injected into both the GPi and the STN bilaterally. 2) The Gi DREADD is injected into the GPi and the Gq DREADD are injected into the STN bilaterally. 3) The Gi DREADD is injected into the GPi and the Gq DREADD are injected into the thalamus bilaterally. 4). The Gq DREADD is injected into the GPe bilaterally.

Example 2: Chemogenetic Treatment of Parkinson's Disease

This set of experiments provide evidence that network abnormalities associated with PD can be corrected by modifying the activity of different nuclei in the basal ganglia loop using Designer Receptors Exclusively Activated by Designer Drugs (DREADD) as describe herein.

Experiments were performed on 2-4 month old wild type C57 black mice. To induce experimental PD, 1 microliter of a solution containing 6 hydroxy dopamine (6-OHDA) (3 mg/1 ml) was injected into the medial forebrain bundle via a small craniotomy drilled in the skull. The mouse head was fixated in a stereotaxic frame, and the 6OHDA containing solution was injected using a glass pipette held by a micromanipulator and a micro-injector.

Mice were anesthetized throughout the procedure with isoflurane. The 6OHDA was injected into the MFB unilaterally or bilaterally to induce bilateral experimental PD.

Shortly after the 6OHDA injection, after recuperation from anesthesia, mice started to rotate in the clockwise direction (ipsilateral to the injection side). Mice were treated with IP glucose and normal saline in the first few days after the 6OHDA injection. In addition, mice had free access to a sucrose solution for the first week after injection. Behavioral experiments were performed at least 3 weeks after the induction of experimental PD.

DREADD Expression:

To express DREADDs (either the inhibitory DREADD Gi or the excitatory DREADD Gq) viral vectors were injected (either AAV8-hSyn-hM3D(Gq)-mCherry or AAV8-hSyn-hM4D(Gi)-mCherry). The viral vectors were injected through a craniotomy with a glass pipette held by a micromanipulator and a micro-injector. During the injections the head was fixated in a stereotaxic frame for accurate injections. Mice were anesthetized throughout the procedure with isoflurane.

The viral vectors (200-500 μl) were injected into several targets in the basal ganglia loop including the STN (either Gi and Gq), the EP and SNr nuclei (Gi), GPe (Gq) and the ventral thalamus (Gq). The injections were usually unilateral at the side of the 6OHDA injections. However, in cases of bilateral 6OHDA injections viral vectors were injected to the target nuclei bilaterally. Usually viral vectors and 6OHDA were injected at the same session.

To confirm the location of DREADD expression, at the end of all experiments the brain was removed and fixated in paraformaldehyde (4%). Few days later the brain was sectioned (100 μm axial sections) with a vibrotome, and DREADD expression was imaged by fluorescent imaging of the fluorescent protein mCherry. Anatomical location of DREADD expression was determined by concomitant bright field imaging of brain sections.

Administration of Clozapine-N-Oxide (CNO) and Normal Saline

To investigate the effect of DREADD activation, 500 μl of either IP CNO (5 mg/kg) or normal saline (NS-0.9% NaCl) was administered. Administration of either CNO or saline was performed in a blinded manner. The vials containing the CNO and NS were label with a numerical code by a second investigator that did not administer the IP dose, nor analyzed behavior. Behavioral experiments were performed approximately 20-30 minutes after IP drug administration.

Behavioral Tests

Two behavioral tests were used for monitoring the behavior of mice: (1) Open field test: Mice were placed in a 30 cm×30 cm×30 cm open top box for 5 minutes and continuous recorded on a video. The results were analyzed off-line after the experiments ended. Using the EthoVision software, the mean velocity and distance traveled by the mice were monitored during the 5 minutes of open field test. In addition, the number and direction of 180° turns were monitored with the EthoVision software. Open field tests were performed on two consecutive days (20-30 minutes after mice received the blinded drug (either NS or CNO)). (2) Rotarod test: Mice were placed on a rotating rod with rotation speed gradually increasing from 4 to 40 RPM using a preset acceleration program. The time mice fell from the rotating rod was measured, with 300 seconds being the maximal time measured on the rod. For each testing session, the rotarod test was performed on 3 consecutive days. During the first day mice underwent 4 training sessions. On the remaining 2 days, mice were tested once a day (20-30 minutes after they received the IP drug (either CNO or NS in a blinded manner)).

The results provided below show improvement of PD motor symptoms obtained by targeting three different nuclei in the basal ganglia loop: the EP (GPi equivalent in primates) and SNr nuclei, which serve as the output nuclei of the basal ganglia loop; the GPe, which is exclusively involved in the indirect pathway; and the STN, which serves as the main target for deep brain stimulation (DBS) in PD patients.

The Entopeduncular Nucleus (EP-Rodent GPi) and the Pars Reticulata of the Substantia Nigra The EP and SNr nuclei serve as the output nuclei of the basal ganglia loop, where the direct, indirect and hyper-direct pathways converge. The aim of this experiment was to treat PD or PD symptoms by inhibiting firing in the SNr and EP nuclei (the rodent equivalent of the primate GPi) using the Gi DREADDS.

Specifically, blinded IP administration of normal saline (NS) and CNO were compared in both hemi-parkinsonian (6-OHDA injected to the MFB) and control mice. The behavioral parameters that were examined included ipsilateral turning and movement velocity in the open field test and time to falling off the rotating rod in the rotarod test.

Figures 1A, 1B:
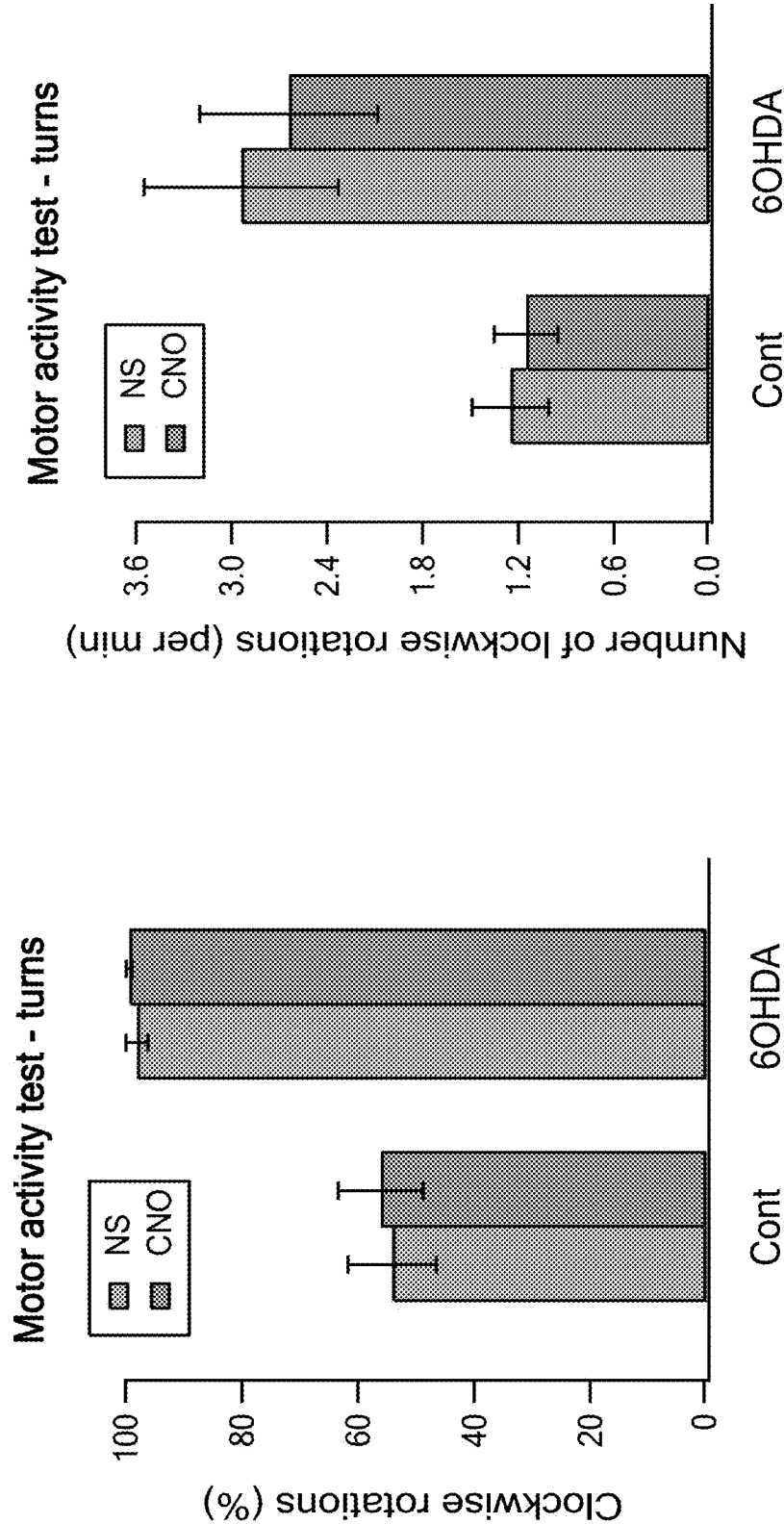
FIGS. 1A-1D. Are bar graphs showing the effect of CNO on normal control mice (Cont) and mice with 6OHDA induced hemi PD (6OHDA). The effect of blinded CNO administration was compared to NS on three behavioral parameters: the number and percent of clockwise rotations in a 5-minute motor activity test (FIG. 1A and FIG. 1B); the mean velocity in a motor activity test (FIG. 1C); and average time mice remained on the rotating rod in the rotarod test (FIG. 1D). CNO had no significant effect on any of these behavioral parameters.
Figures 1C, 1D:
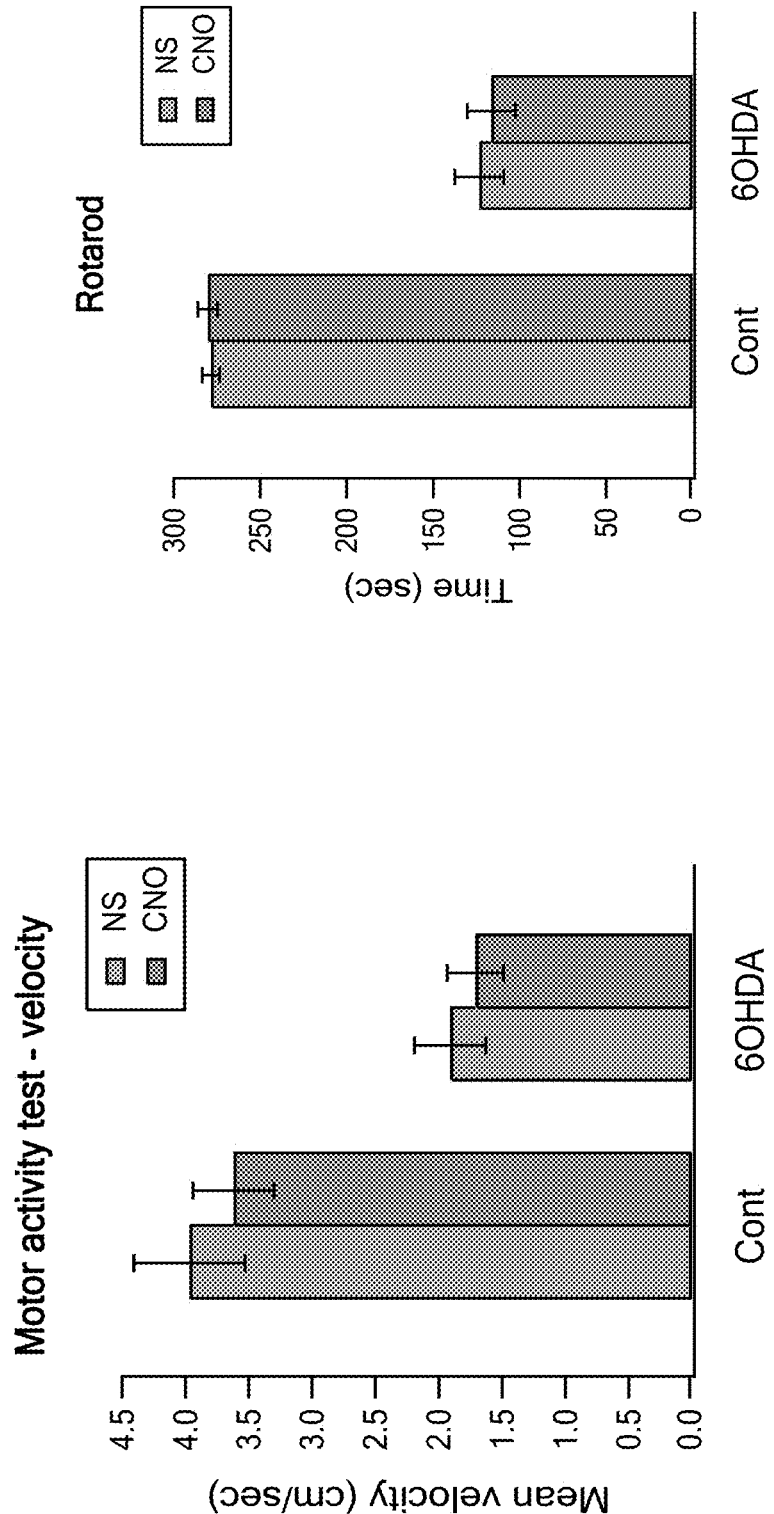

In normal control and mice with experimental 6OHDA induced hemi PD no significant differences between blinded IP administration of CNO and NS were observed on any of the three behavioral parameters we examined (FIG. 1).

Figure 2C:
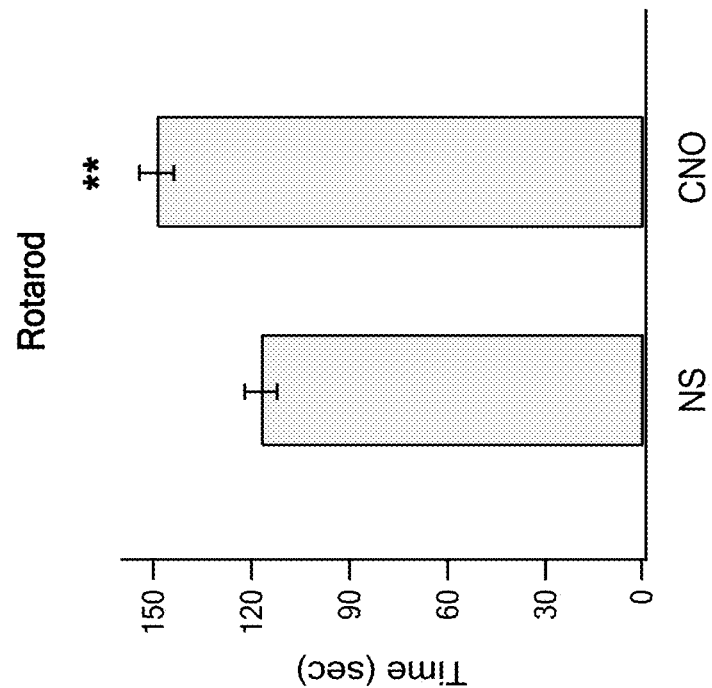
Figure 2D:
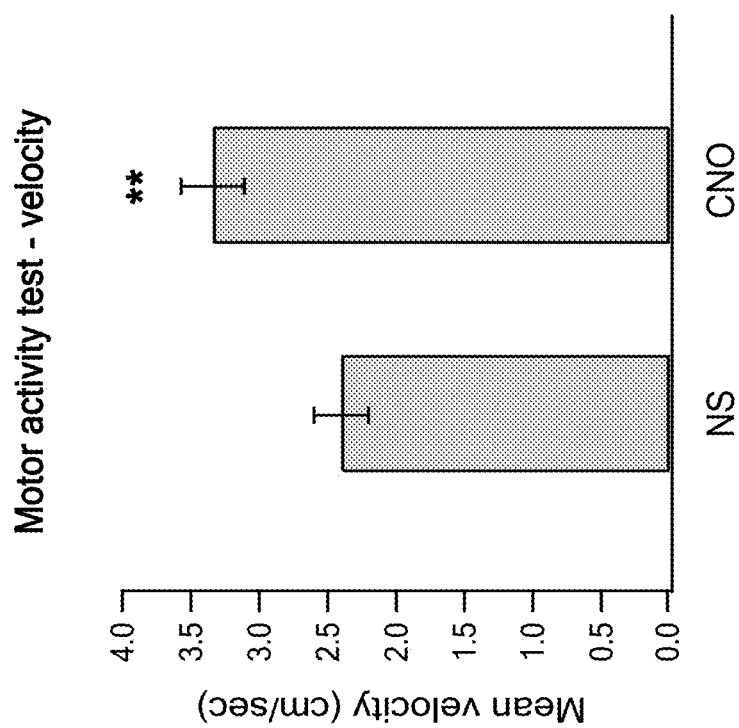

In contrast, in mice with 6OHDA induced hemi PD mice and expressing Gi DREADDS in the EP and SNr nuclei blinded CNO application resulted in significantly and surprisingly better behavioral performances compared to NS in all behavioral parameters examined. As compared to NS, CNO caused a 36±9% improvement in the mean velocity in the open field test; a 68.9±10.8% reduction in the number and 46±8.6% reduction in the percent of clockwise rotations; and a 30.5±7.1% increase in the time spent on the rotating rod in the rotarod test (FIG. 2).

Targeting the External Globus Pallidum Nucleus (GPe)

In this set of experiments, the GPe nucleus, which serves as a major relay nucleus exclusively belonging to the indirect pathway, was targeted. More specifically, the GPe neurons were activated using the excitatory Gq DREADDs, and the effect on behavior on 6-OHDA induced hemi-parkinsonian mice, was monitored.

Figure 4A:
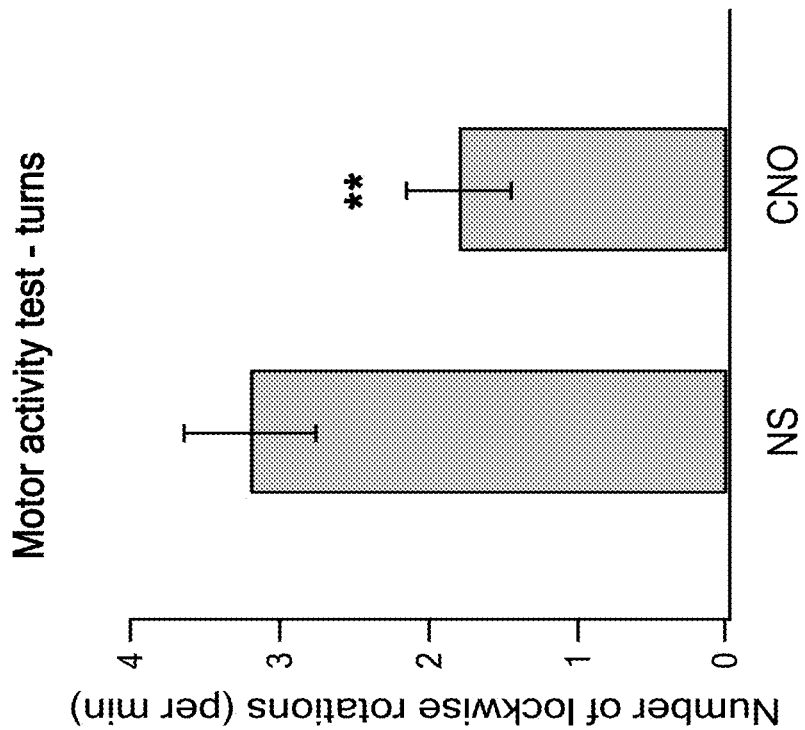
FIGS. 4A-4D. Are bar graphs showing the effect of unilateral Gq DREADDs in the GPe—the effect of CNO on 6OHDA induced hemi PD expressing the Gq DREADD in the GPe nucleus. The effect of blinded CNO administration was compared to NS on three behavioral parameters: the number and percent of clockwise rotations in a 5-minute motor activity test (FIG. 4A and FIG. 4B); the mean velocity in the motor activity test (FIG. 4C); and average time mice remained on the rotating rod in the rotarod test (FIG. 4D). The beneficial effect of CNO on all behavioral parameters examined. ** $p<0.01$.
Figure 4B:
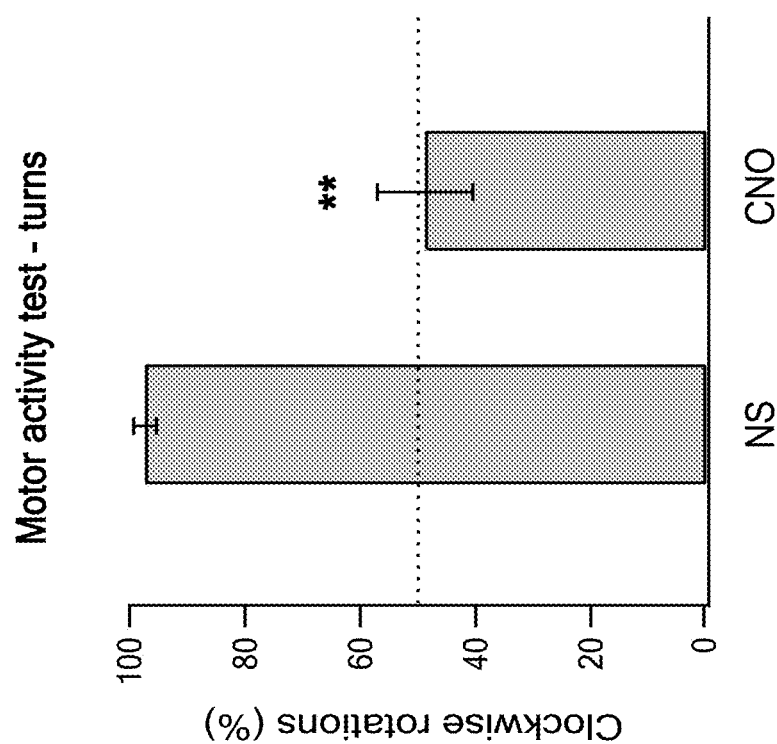
Figures 4C, 4D:
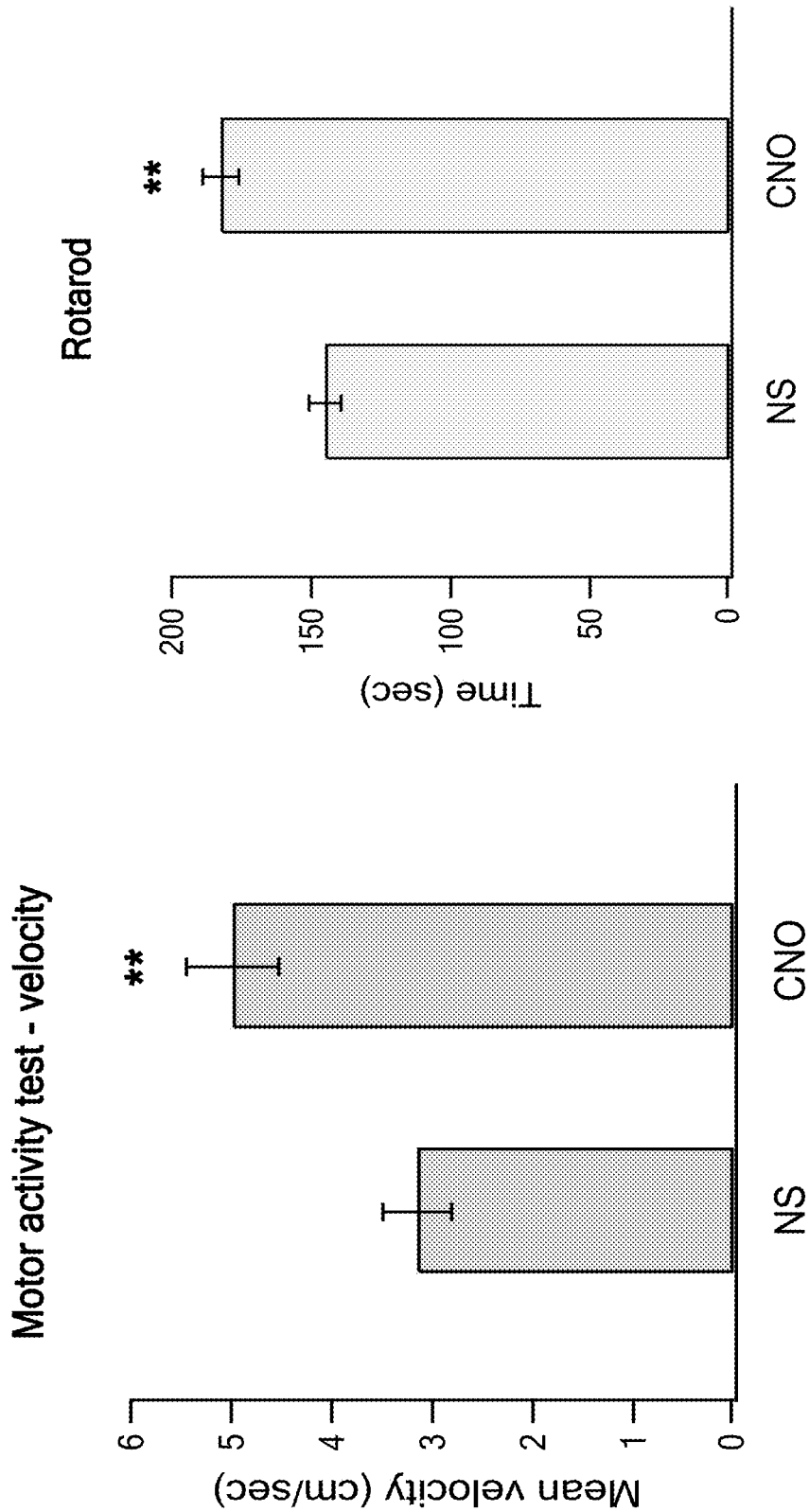
Figure 5B:
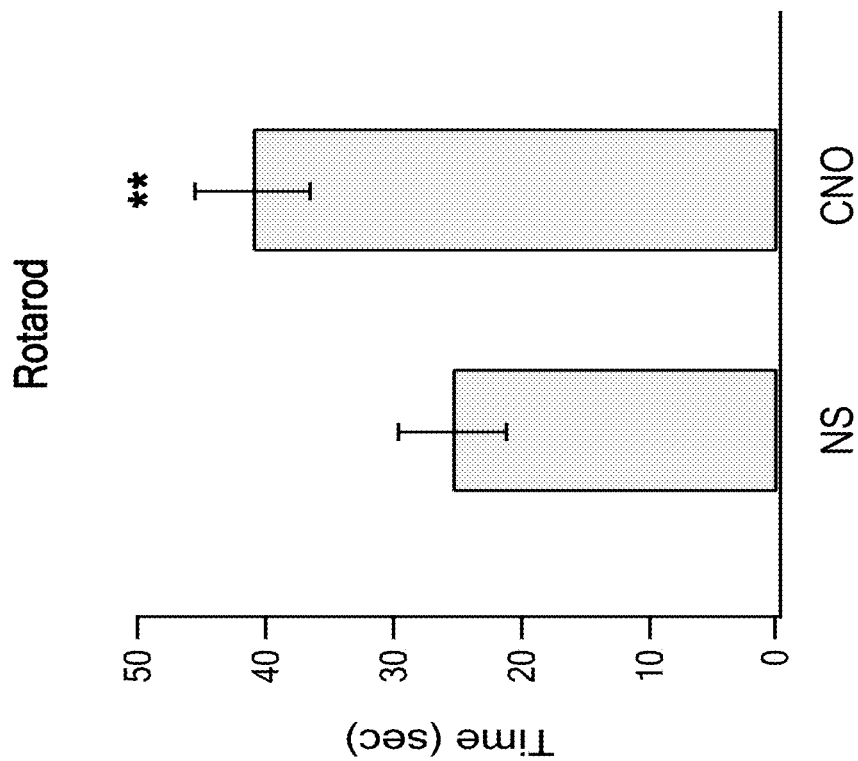
FIGS. 5A-5B. Are bar graphs showing the effect of bilateral Gq DREADDs in the GPe—the effect of CNO on 6OHDA induced bilateral PD expressing the Gq DREADD in both Gpe nuclei. The effect of blinded CNO administration was compared to NS on two behavioral parameters: The mean velocity in a motor activity test (FIG. 5A); and the average time mice remained on the rotating rod in the rotarod test (FIG. 5B). The beneficial effect of CNO on both the mean velocity and rotarod test. ** $p<0.01$.
Figure 5A:
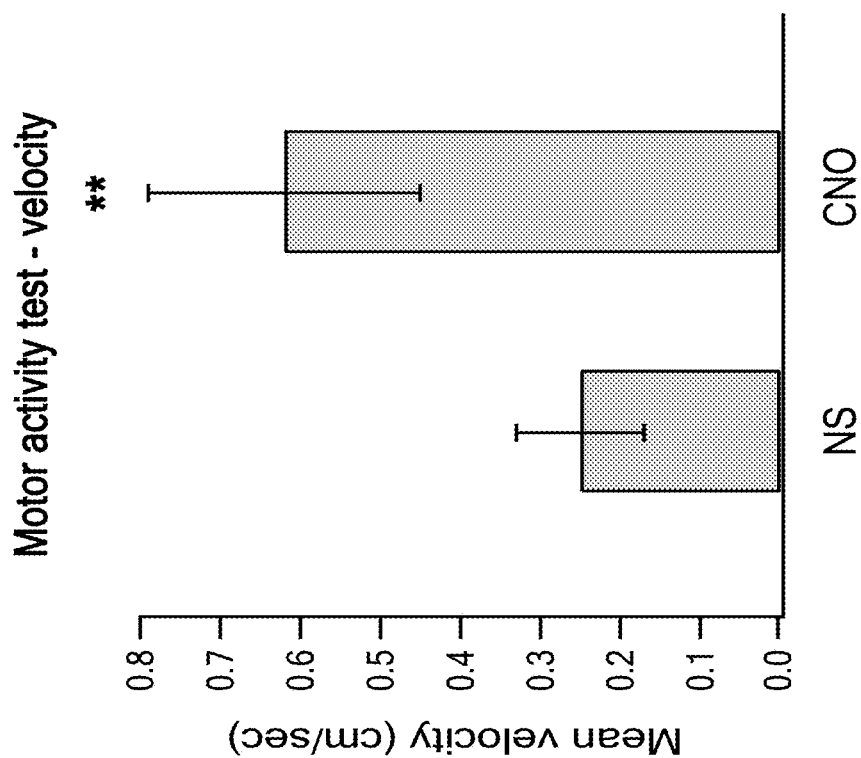
Figure 6B:
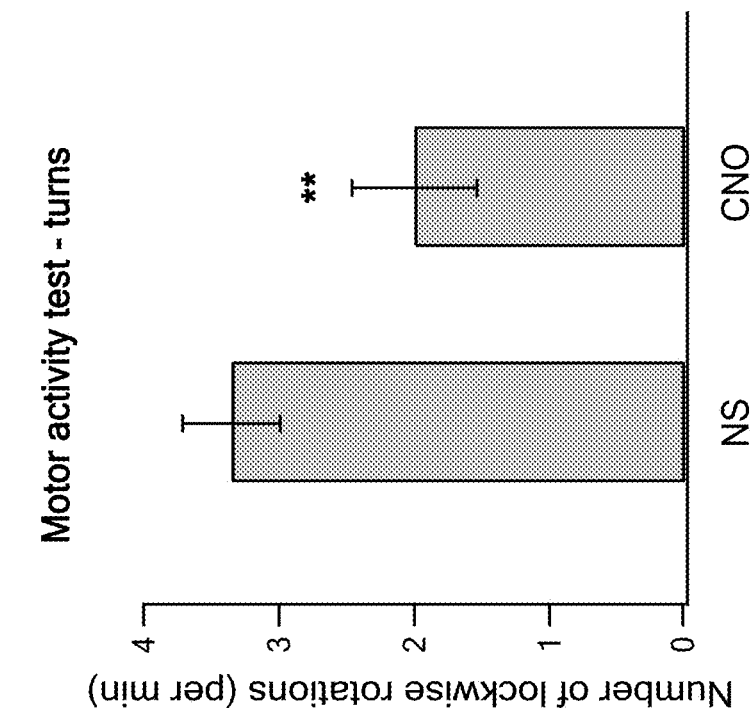
FIGS. 6A-6D. Are bar graphs showing the effect of unilateral Gq DREADDs in the STN—the effect of CNO on 6OHDA induced hemi PD expressing the Gq DREADD in the STN nucleus. The effect of blinded CNO administration was compared to NS on three behavioral parameters: the number and percent of clockwise rotations in a 5-minute motor activity test (FIG. 6A and FIG. 6B); the mean velocity in the motor activity test (FIG. 6C); and average time mice remained on the rotating rod in the rotarod test (FIG. 6D). Note the beneficial effect of CNO on turns and mean velocity, but not in the rotarod test. ** $p<0.01$.
Figure 6A:
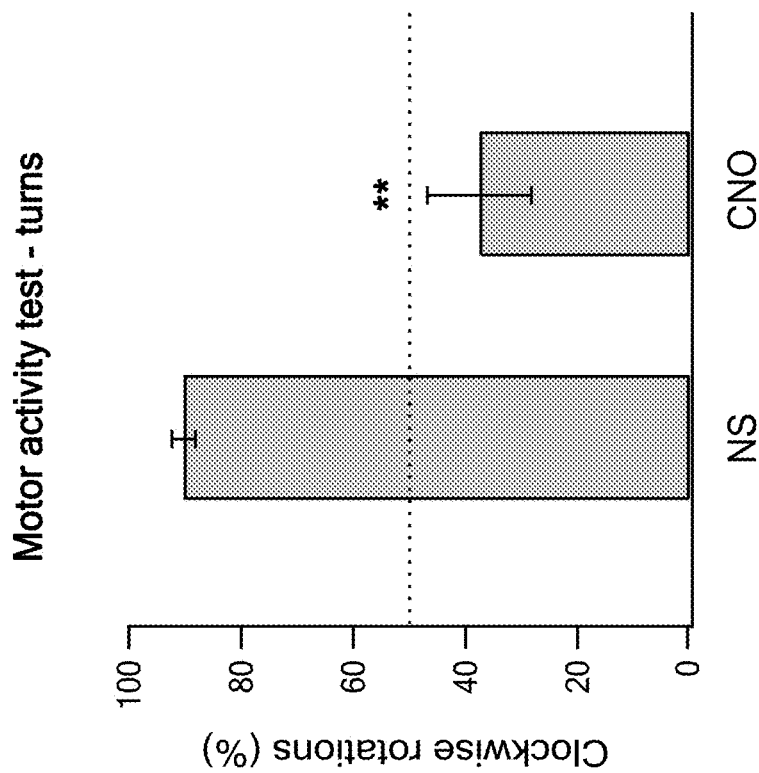
Figure 6D:
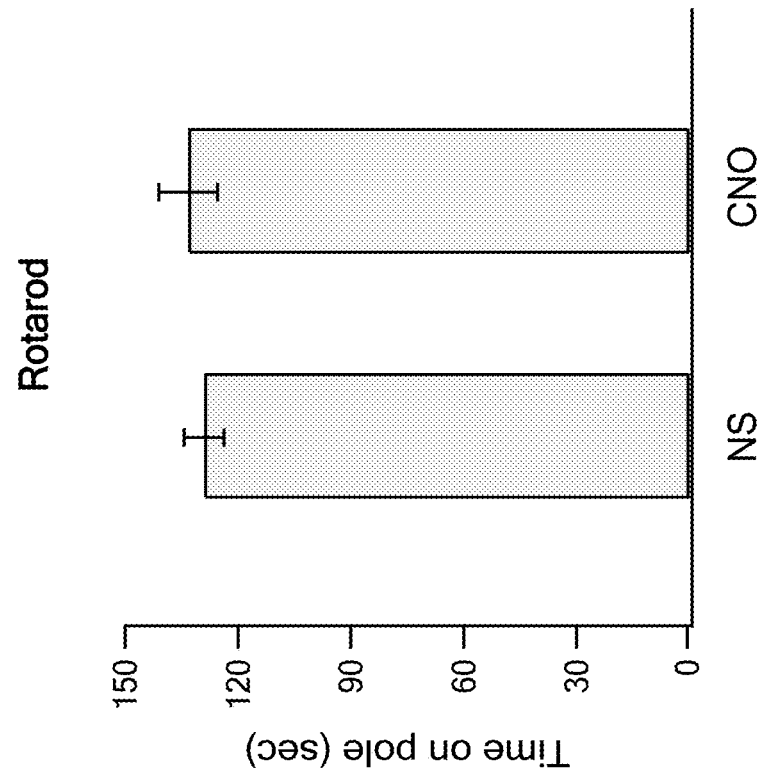
Figure 6C:
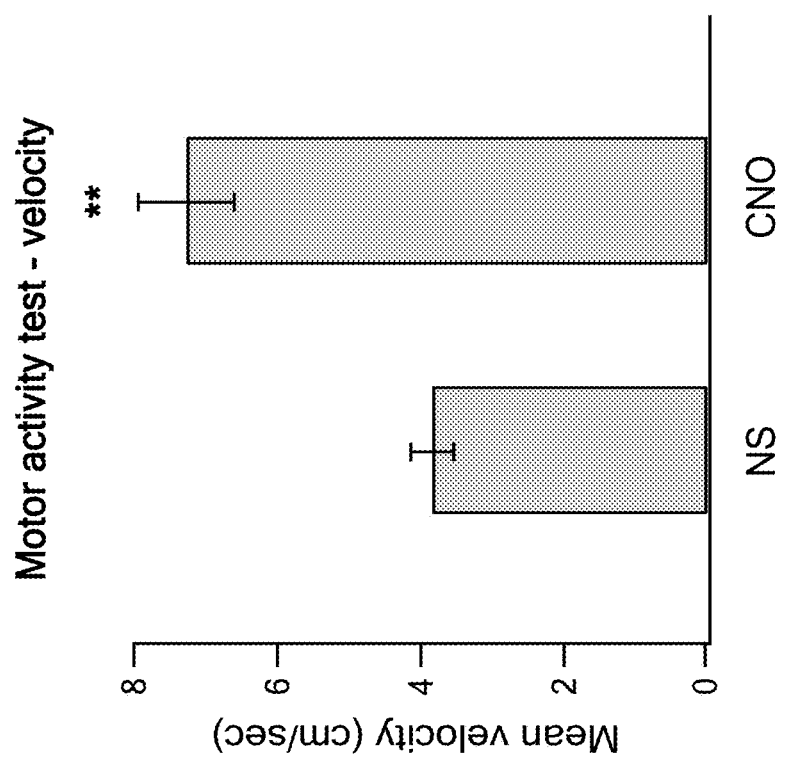

These experiments showed that blinded administration of CNO resulted in a significant improvement of all behavioral parameters as compared to normal saline (NS) interperitoneally (IP) administered. CNO administration resulted in an increase of 77.2±24.7% in the mean velocity in the open field test; a 37.7±20% reduction in the number and 40±7.8% reduction in the percent of clockwise rotations; and a 25.6±6.1% increase in the time spent on the rotating rod in the rotarod test (FIG. 4). Thus suppressing the activity of the indirect pathway by DREADD-mediated activation of the GPe nucleus significantly improved performances of all motor parameters examined in both unilateral and bilateral 6-OHDA-induced PD mice. The effects of DREADD-mediated activation of the GPe on motor performance and/or function were more pronounced in the case of bilateral 6-OHDA induced PD (Gq DREADDs were expressed uni- and bilaterally in the GPe of hemi- and bilateral parkinsonian mice, respectively).

The Sub Thalamic Nucleus (STN)

In contrast to the GPe nucleus, STN neurons participate in both the indirect and hyper direct pathways. The effect of both inhibitory or excitatory DREADDs expressed in the STN on behavior of experimental 6OHDA induced PD was tested.

When the effect of blinded IP administration of CNO to NS was compared on the open field and rotarod tests, it was found that activation of Gi expressed in the STN did not significantly affect the mean velocity nor performances in the rotarod test. Activation of Gi DREADDs expressed in the STN nucleus did show a small, yet significant beneficial effect on turns.

In contrast, activation of Gq DREADDS expressed in the STN had large, unexpected and significant beneficial effects on 6-OHDA experimental PD. CNO administration resulted in an increase of 117.6±26.9% in the mean velocity in the open field test; a 37.2±17% reduction in the number and 47.6±11.1% reduction in the percent of clockwise rotations. The performances in the rotarod test showed no significant differences between blinded CNO and NS application in this group (FIG. 6).

Figure 7B:
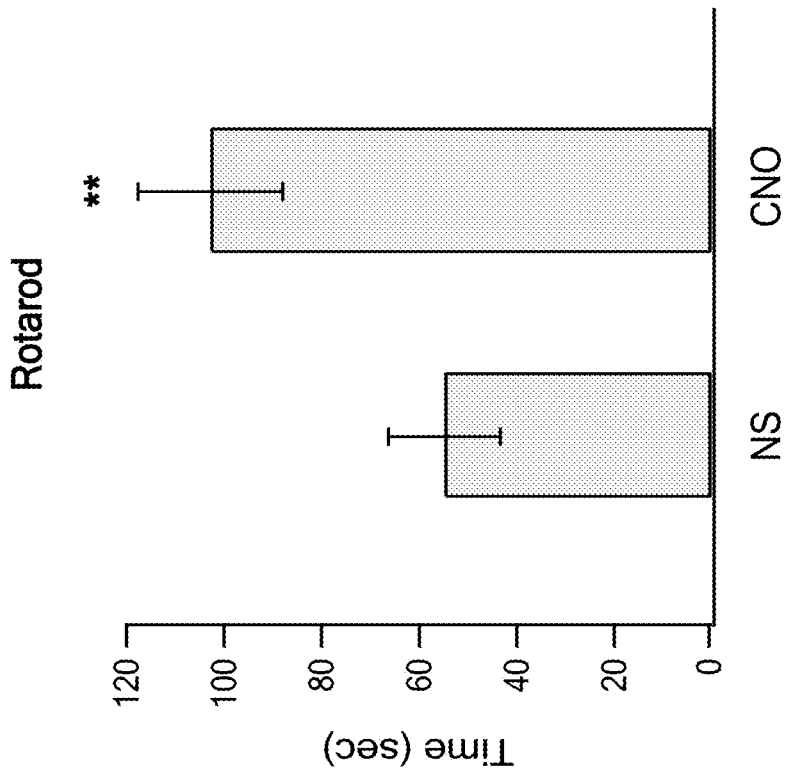
FIGS. 7A-7B. Are bar graphs showing the effect of bilateral Gq DREADDs in the STN—the effect of CNO on 6OHDA induced bilateral PD expressing the Gq DREADD in both STN nuclei. The effect of blinded CNO administration was compared to NS on two behavioral parameters: The mean velocity in a motor activity test (FIG. 7A); and the average time mice remained on the rotating rod in the rotarod test (FIG. 7B). The beneficial effect of CNO on both the mean velocity and rotarod test. ** $p<0.01$.
Figure 7A:
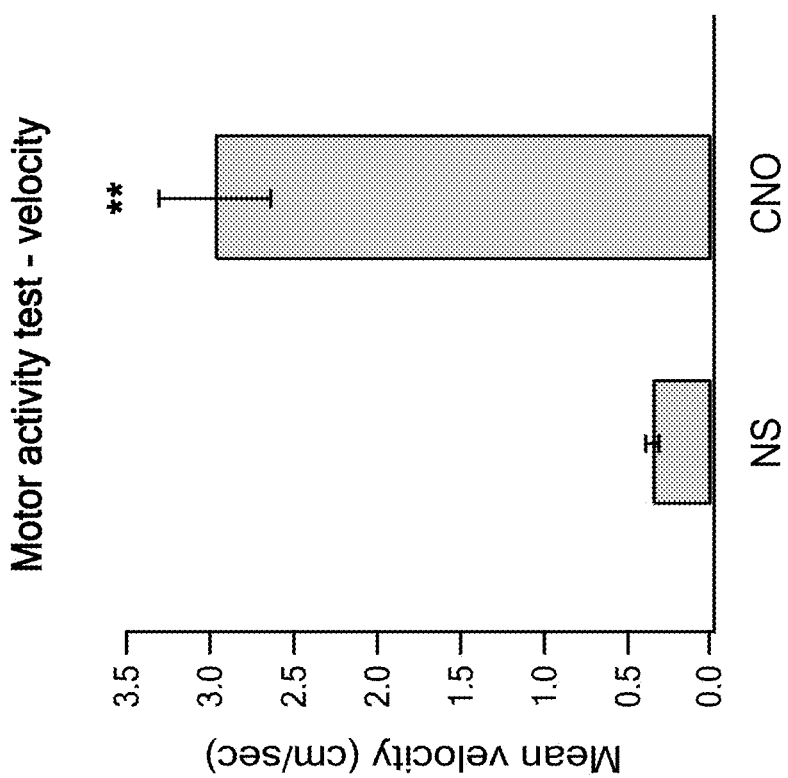

In addition, the effect of bilateral Gq activation on bilateral experimental PD (6OHDA injected to the MFB bilaterally), was tested. It was found that Gq activation in these mice had a dramatic unexpected effect. CNO administration resulted in a 294.4±70.9% increase in the mean velocity in the open field test and an 81±15.8% increase in the time before falling off the rotarod (FIG. 7). In this case turns were not analyzed as to begin with mice with bilateral experimental PD showed little tendency to rotate to either side (0.1±0.06 turns per minute).

Figure 8A:
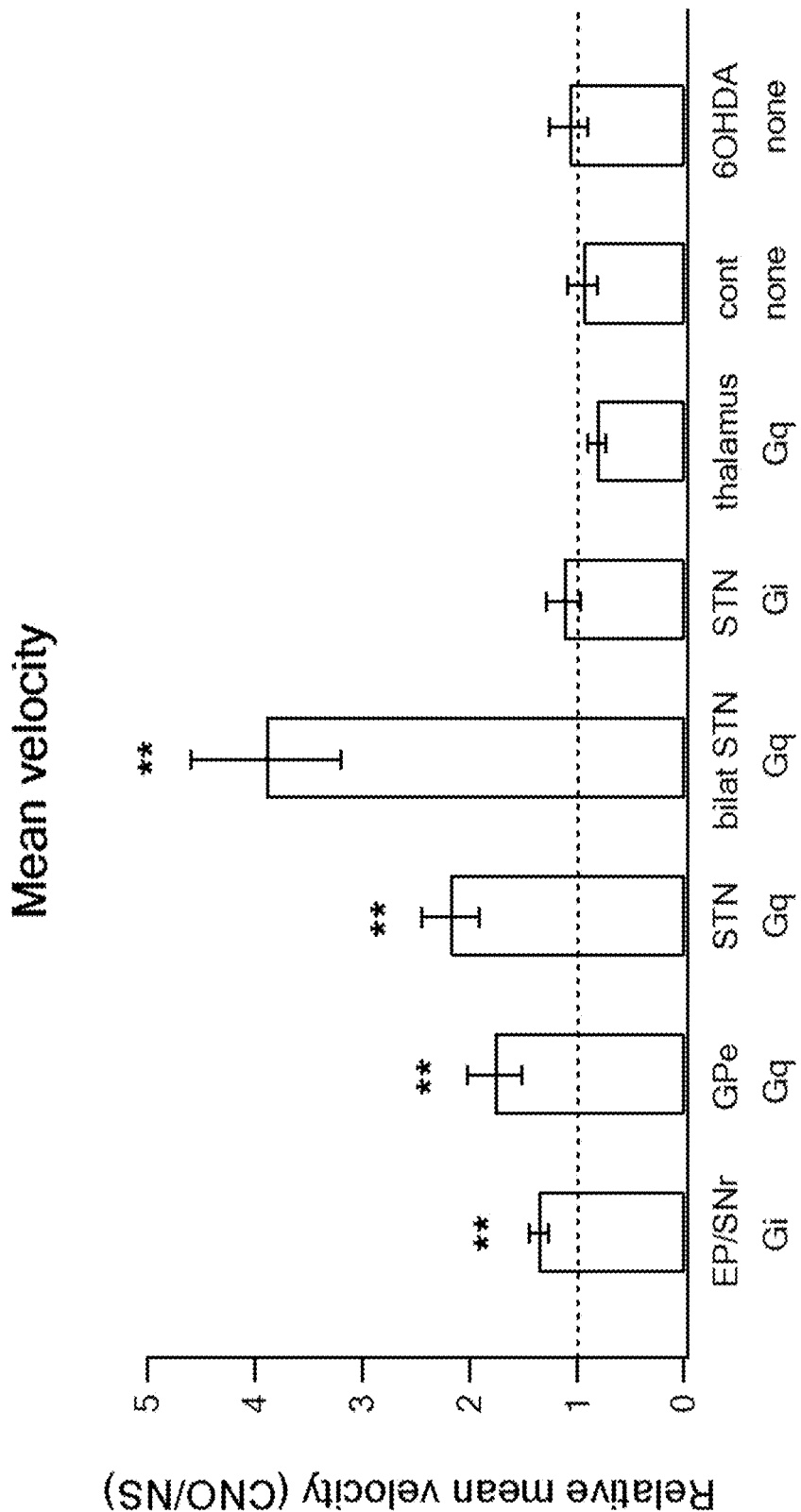
FIGS. 8A-8C. Are bar graphs summarizing the effect of CNO on mice with 6OHDA induced experimental PD expressing DREADDs in different nuclei: Gi in the EP and SNr nuclei, Gq in the GPe nucleus, Gq in the STN, Gq in both STN nuclei (upper 2 panels), Gi in the STN, Gq in the ventral thalamus, control mice and mice with 6OHDA induced hemi PD. The relative effect of CNO and NS (CNO/NS) is presented for three behavioral parameters: The mean velocity in a motor activity test (FIG. 8A); the time mice remained on the rotating rod in the rotarod test (FIG. 8B); and the reduction in the percent of clockwise rotations in a 5-minute motor activity test (FIG. 8C). ** $p<0.01$.
Figure 8B:
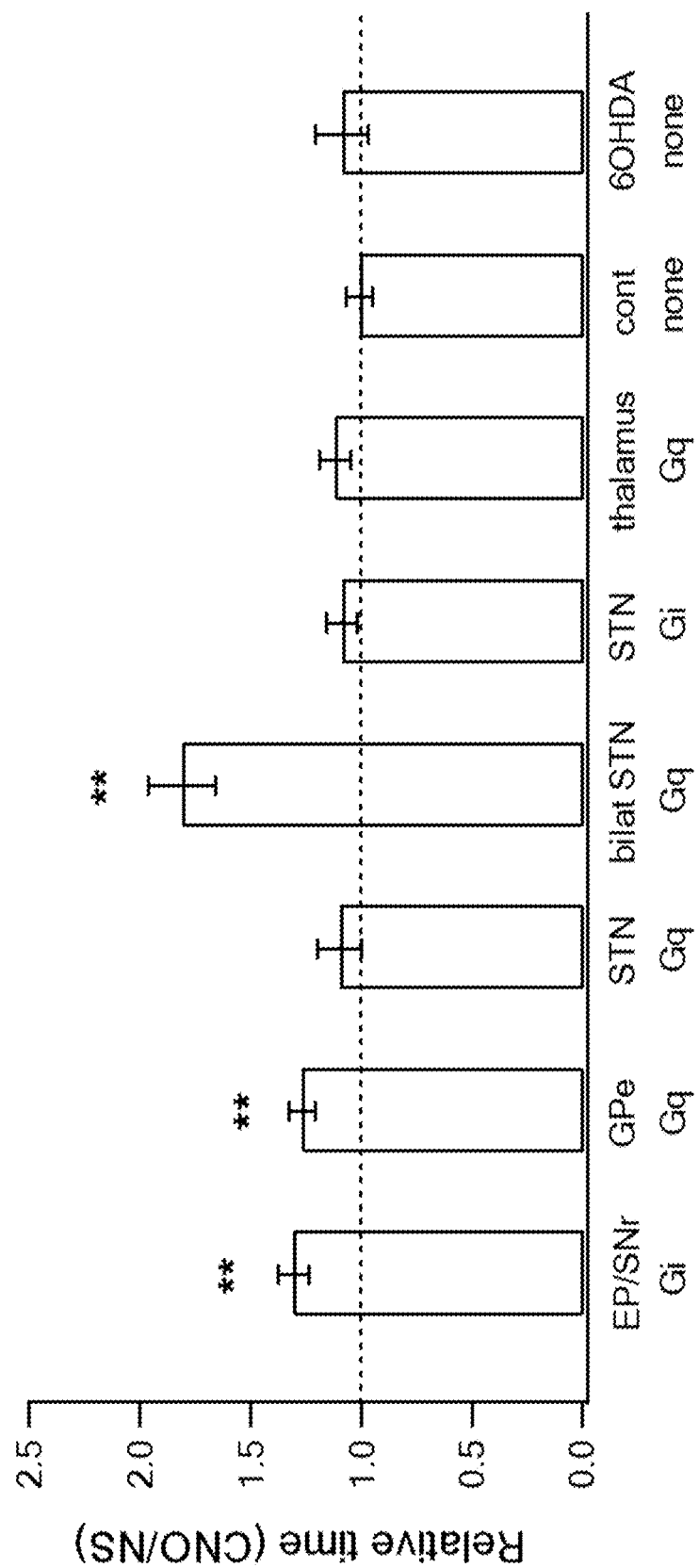
Figure 8C:
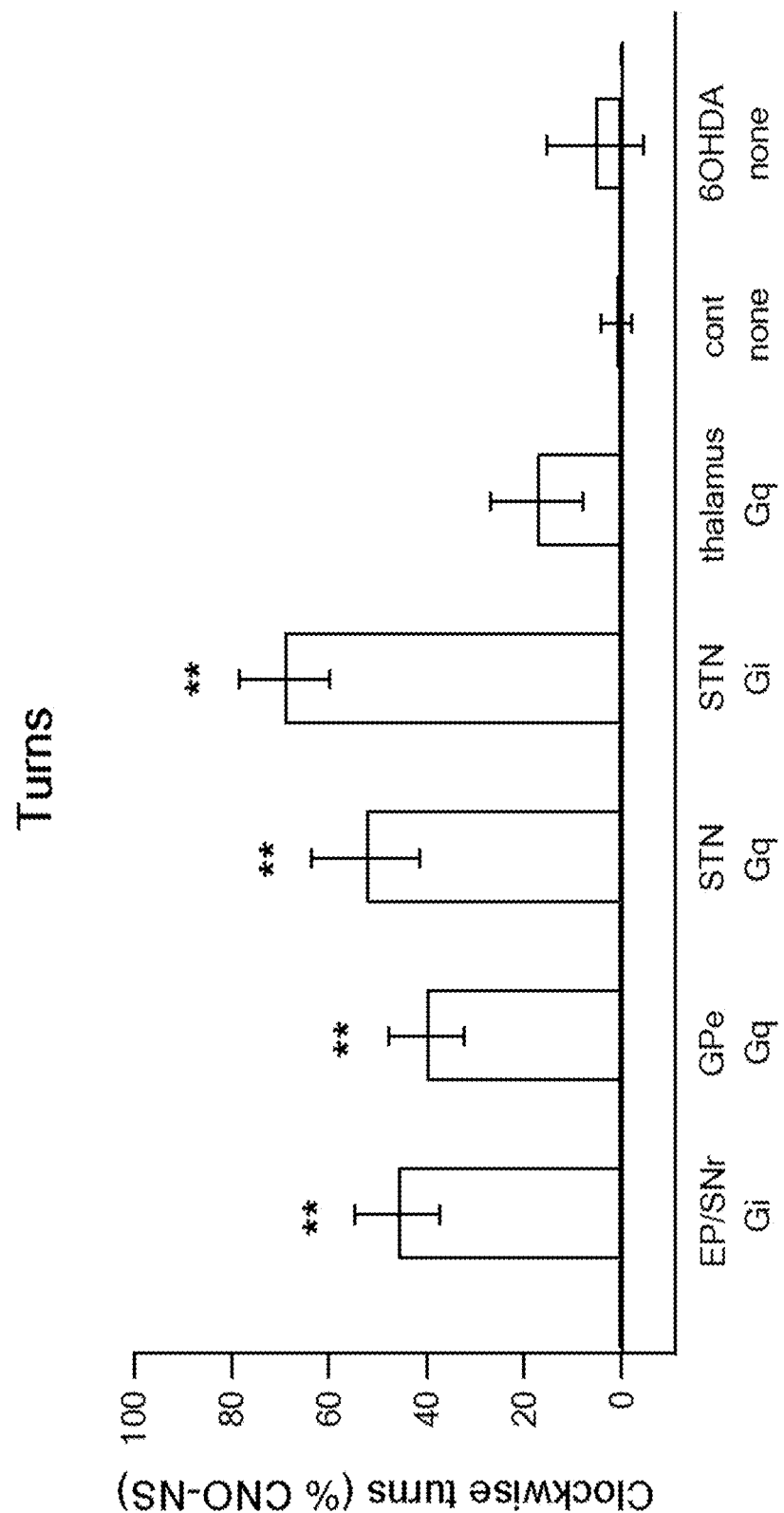

FIG. 8 presents a comparison between the different DREADD mediated manipulations that were performed in these experiments.

Combined Suppression of the Output Nuclei and Indirect Pathway

The results obtained in this section further support the findings provided hereinabove. In this set of experiments the NS and CNO were applied intraperitoneally daily for 5 consecutive days. The open field test was performed on day 2 and 4 (for both CNO and NS groups). Rota-Rod test was performed on days 3 and 5. The results of the motor velocity, rotations and Rota-Rod scores were compared between the normal saline and CNO application.

The following conditions were examined. Further support for the impact of suppression of the output nuclei: activation of Gi via DREADDs in the GPi and SNR nuclei in hemi-parkinsonian mice is provided in FIG. 9. Further support for the impact of suppression of the indirect pathway on motor activity by Activation of Gq DREADDs in the GPe nucleus in hemi-parkinsonian mice is provided in FIG. 10. Evidence for the impact of combined suppression of the output nuclei and indirect pathway and activation of the STN via simultaneous Activation of Gi DREADDs in the GPi and SNR nuclei, of Gq DREADDs in the GPe nucleus and of Gq DREADDs in the STN is provided in FIG. 11.

These sets of experiments demonstrate that targeting different nuclei and pathways within the basal ganglia complex in experimental Parkinson's disease result in unexpected improved motor performance and/or function of experimental PD. Specifically, suppressing the activity of the indirect pathway by targeting the GPe nucleus; activating the STN; and suppressing the output activity of the basal ganglia by targeting the output nuclei the GPi and SNr resulted in an unprecedented restoration and/or improvement of motor performance and/or function in mice afflicted with PD.

What is claimed is:

1. A method for treating a subject afflicted with: (A) a neuronal hypo-kinetic disease or disorder; and (B) partial or complete loss of muscle movement due to a disruption in the basal ganglia, comprising concomitantly though the use of a single ligand:
   (a) suppressing neuronal activity in the internal globus pallidus (GPi); and
   (b) enhancing neuronal activity in: the anterior motor thalamus, the external globus pallidum (GPe), and/or the subthalamic nucleus (STN); wherein said suppressing neuronal activity comprises transfecting a GPi neuron with an inhibitory DREADD and activating said inhibitory DREADD, wherein said enhancing neuronal activity comprises transfecting a neuron in: the anterior motor thalamus, the external globus pallidum (GPe), and/or the subthalamic nucleus (STN), with excitatory DREADD and activating said excitatory DREADD, thereby treating a subject afflicted with a neuronal hypo-kinetic disease or disorder and partial or complete loss of muscle movement due to a disruption in the basal ganglia.

2. The method of claim 1, wherein said transfecting GPi neuron with an inhibitory DREADD is injecting AAV viral vector comprising the Gi DREAD gene.

3. The method of claim 1, wherein said transfecting neuron in: the anterior motor thalamus, the external globus pallidum (GPe), or the subthalamic nucleus (STN) with an excitatory DREADD is injecting AAV viral vector comprising the: Gq DREAD gene, Gs DREAD gene, or both.

4. The method of claim 1, wherein said activating said inhibitory DREADD, is contacting said GPi neuron with CNO, wherein said activating said excitatory DREADD is contacting an anterior motor thalamus neuron, a GPe neuron, and/or a STN neuron, with CNO.

5. The method of claim 1, wherein said treating a subject afflicted with hypo-kinetic disease or disorder is improving motor activities in said subject.

6. The method of claim 1, wherein said treating a subject afflicted with hypo-kinetic disease or disorder is alleviating non-motor symptoms associated with Parkinson's disease.

7. The method of claim 1, wherein said treating a subject afflicted with hypo-kinetic disease or disorder is without inducing permanent damage to the brain.

8. The method of claim 1, wherein said neuronal hypo-kinetic disease or disorder is Parkinson's disease.

* * * * *